United States Patent [19]
Jarreau et al.

[11] Patent Number: 5,171,747
[45] Date of Patent: Dec. 15, 1992

[54] 3-ARYLOXAZOLIDINONE DERIVATIVES, PROCESS FOR THEIR PREPARATION AND THEIR USE IN THERAPY

[75] Inventors: Francois X. Jarreau, Versalles; Vincenzo Rovei, Rueil Malmaison; Jean-Jacques Koenig, Maisons Laffitte; Alain R. Schoffs, Paris, all of France

[73] Assignee: Delalande S.A., Courbevoie, France

[21] Appl. No.: 598,254

[22] Filed: Oct. 16, 1990

[30] Foreign Application Priority Data

Oct. 17, 1989 [FR] France ............................ 89 13555

[51] Int. Cl.⁵ .................... C07D 263/24; A61K 31/42
[52] U.S. Cl. .................................. 514/376; 548/110; 548/216; 548/231; 548/232; 549/221; 549/332; 549/449; 549/451; 549/452; 549/453; 549/455; 556/413; 556/422; 564/443; 568/623; 568/624
[58] Field of Search ................. 548/231, 232; 514/376

[56] References Cited

U.S. PATENT DOCUMENTS

| | | | |
|---|---|---|---|
| 4,250,318 | 2/1981 | Dostert et al. | 548/229 |
| 4,348,393 | 9/1982 | Bourgery et al. | 548/182 |
| 4,517,197 | 5/1985 | Ancher et al. | 514/376 |
| 5,036,090 | 7/1991 | Jarreau et al. | 514/376 |
| 5,036,091 | 7/1991 | Jarreau et al. | 514/376 |

OTHER PUBLICATIONS

Ancher et al., Chemical Abstracts, vol. 95, No. 132868 (Abstract for FR 2458547, Jan. 2, 1981).

Primary Examiner—Mukund J. Shah
Assistant Examiner—E. Bernhardt
Attorney, Agent, or Firm—Zarley, McKee, Thomte, Voorhees & Sease

[57] ABSTRACT

The derivatives of the formula:

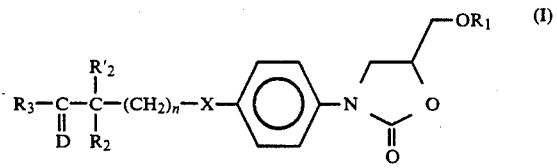

wherein:
$R_1$ is H or $C_1$-$C_4$ alkyl;
X is an oxygen atom, a methylene group or a —CH=CH— group;
n is 1 or 2 when X is an oxygen atom or a methylene group and 0 or 1 when X is a —CH=CH— group;
D is an oxygen atom or a NOR group, wherein R=H or $C_1$-$C_4$ alkyl;
$R_3$ is a $C_1$-$C_4$ alkyl, $C_3$-$C_7$ cycloalkyl, phenyl or benzyl group;
each of $R_2$ and $R'_2$ independently is a hydrogen atom or a $C_1$-$C_4$ alkyl, $C_3$-$C_7$ cycloalkyl, phenyl or benzyl group; and
$R'_2$ and $R_3$ may further form together a —(CH$_2$)$_3$— or —(CH$_2$)$_4$— chain, useful as drugs.

10 Claims, No Drawings

3-ARYLOXAZOLIDINONE DERIVATIVES, PROCESS FOR THEIR PREPARATION AND THEIR USE IN THERAPY

The present invention relates to new 3-aryl-2-oxazolidinone derivatives, to a process for their preparation and to their use in therapy.

More precisely, these derivatives correspond to the formula:

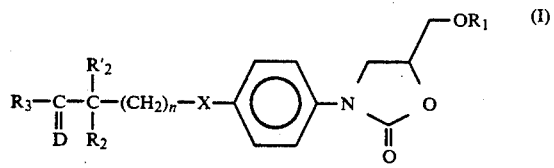

wherein:

$R_1$ is H or $C_1$-$C_4$ alkyl;

X is an oxygen atom, a methylene group or a —CH═CH— group;

n is 1 or 2 when X is an oxygen atom or a methylene group and 0 or 1 when X is a —CH═CH— group;

D is an oxygen atom or a NOR group, wherein R═H or $C_1$-$C_4$ alkyl;

$R_3$ is a $C_1$-$C_4$ alkyl, $C_3$-$C_7$ cycloalkyl, phenyl or benzyl group;

each of $R_2$ and $R'_2$ independently is a hydrogen atom or a $C_1$-$C_4$ alkyl, $C_3$-$C_7$ cycloalkyl, phenyl or benzyl group; and $R'_2$ and $R_3$ may further form together a —(CH$_2$)$_3$— or —(CH$_2$)$_4$— chain.

It should be moreover noted that the derivatives (I) include one or more asymmetric carbon atoms. They can therefore be under the form of diastereoisomers or enantiomers or under the cis- or trans-form or also under the form of a mixture of all theses forms, including the racemic forms. The present invention therefore encompasses the various forms so defined, with the exclusion of the racemates of formule (I) wherein $R_1$=CH$_3$, X=oxygen, $R_2$=$R'_2$=H, n=1 or 2 and D=oxygen.

The above formula (I) particularly encompasses the derivatives for which:

$R_1$=H or CH$_3$;
X=oxygen or CH$_2$;
n=1 or 2;
$R_2$=$R'_2$=H or CH$_3$;
$R_3$=$C_1$-$C_4$ alkyl; and
D is oxygen, N—OH or N—OCH$_3$.

The derivatives for which:
$R_1$=CH$_3$;
X=oxygen;
n=1 or 2;
$R_2$=$R'_2$=H;
$R_3$=CH$_3$; and
D is oxygen;

the derivatives for which:
$R_1$=CH$_3$;
X=oxygen;
n=1 or 2;
$R_2$=$R'_2$=H;
$R_3$=CH$_3$; and
D is (E) N—OH;

the derivatives for which:
$R_1$=CH$_3$;
X=methylene;
n=1 or 2;
$R_2$=$R'_2$=H;
$R_3$=CH$_3$; and
D is oxygen;

the derivatives for which:
$R_1$=CH$_3$;
X=methylene;
n=1 or 2;
$R_2$=$R'_2$=H;
$R_3$=CH$_3$; and
D is (E) N—OH;

| the derivatives for which: | the derivatives for which: |
|---|---|
| $R_1$ = CH$_3$; | $R_1$ = CH$_3$; |
| X represents CH═CH; | X represents CH═CH; |
| n = 0 or 1; | n = 0 or 1; |
| $R_2$ = $R'_2$ = H; | $R_2$ = $R'_2$ = H; |
| $R_3$ = CH$_3$; and | $R_3$ = CH$_3$; and |
| D represents oxygen, and | D represents (E)N—OH | are particularly mentioned.

The present invention moreover relates to the preparation processes of derivatives (I).

These processes are mainly based on two general synthetic routes.

The first one of these routes comprises creating an entity including the 2-oxazolidinone moiety (schemes 1 and 2), following by grafting on this entity a chain including a precursor group of >C═D (schemes 3 to 6), and lastly transforming this precursor group in >C═D (scheme 7).

Conversely, the second one of these routes comprises firstly creating the chain including the precursor group of >C═D (schemes 8 to 11), followed by creating and grafting on this chain an entity including the 2-oxazolidinone moiety (schemes 12 to 14), and lastly transforming the precursor group in >C═D (scheme 7).

These fourteen schemes are represented below. Unless otherwise stated, the symbols $R_1$, X, n, $R_2$, $R'_2$, $R_3$ and R appearing in these schemes have the same meaning as in formula (I).

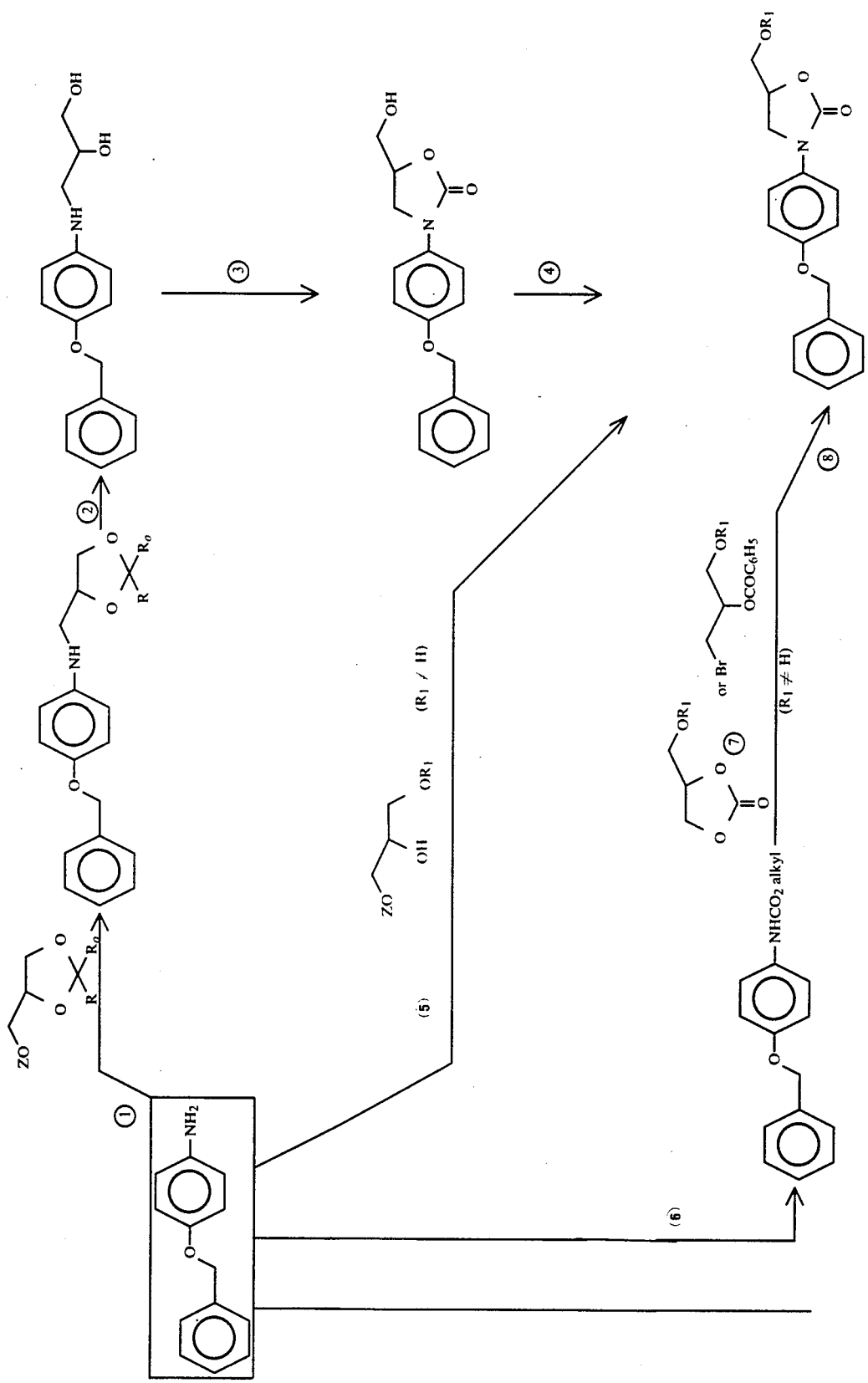

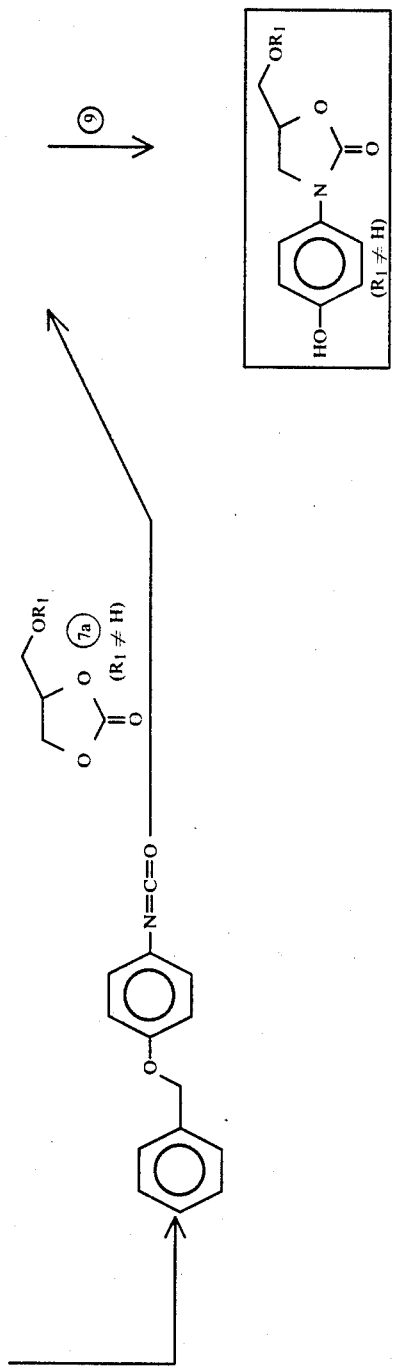
-continued
Scheme 1
Z = Ms Or Ts
each of R and R₀ is C₁-C₃ alkyl or
R and R₀ form togetyher —(CH₂)₅—

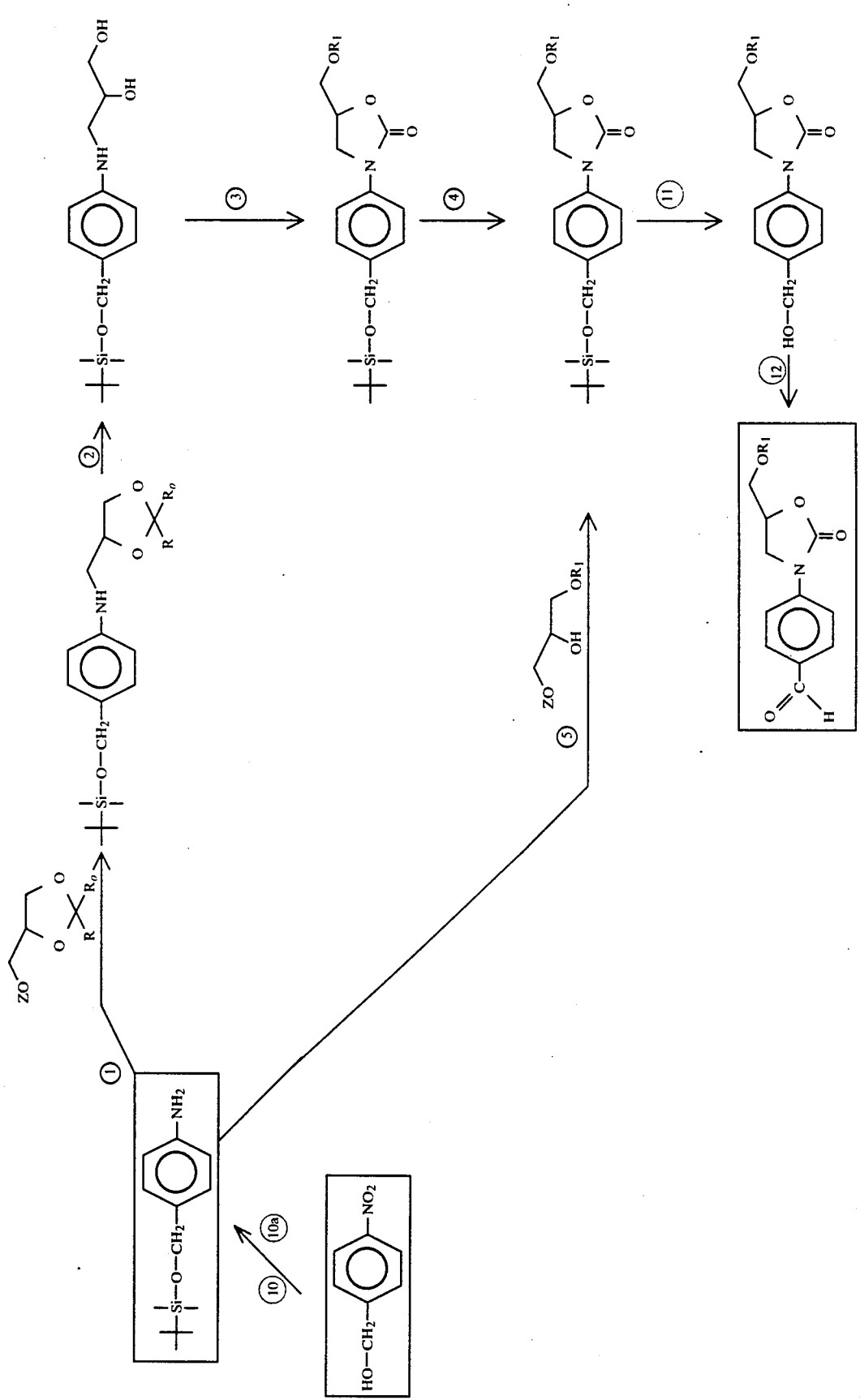
Scheme 2
$R_1 \neq H$
$Z = Ts$ or $Ms$
each of $R$ and $R_0$ is $C_1-C_3$ alkyl
or $R$ and $R_0$ form together $-(CH_2)_5-$ Scheme 3
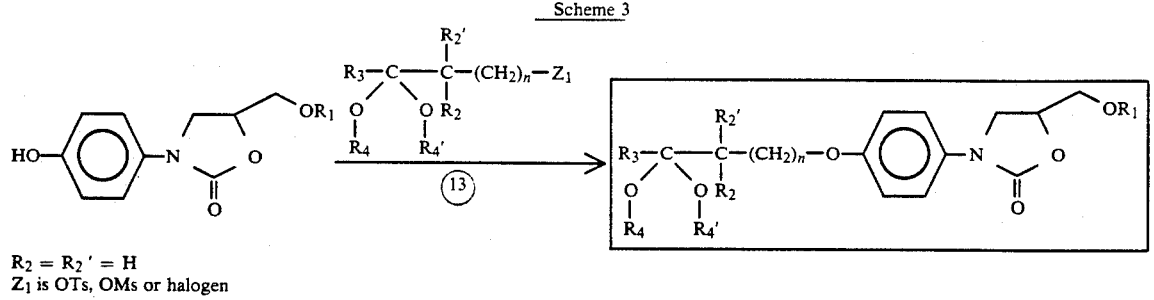
$R_2 = R_2' = H$
$Z_1$ is OTs, OMs or halogen
Scheme 4
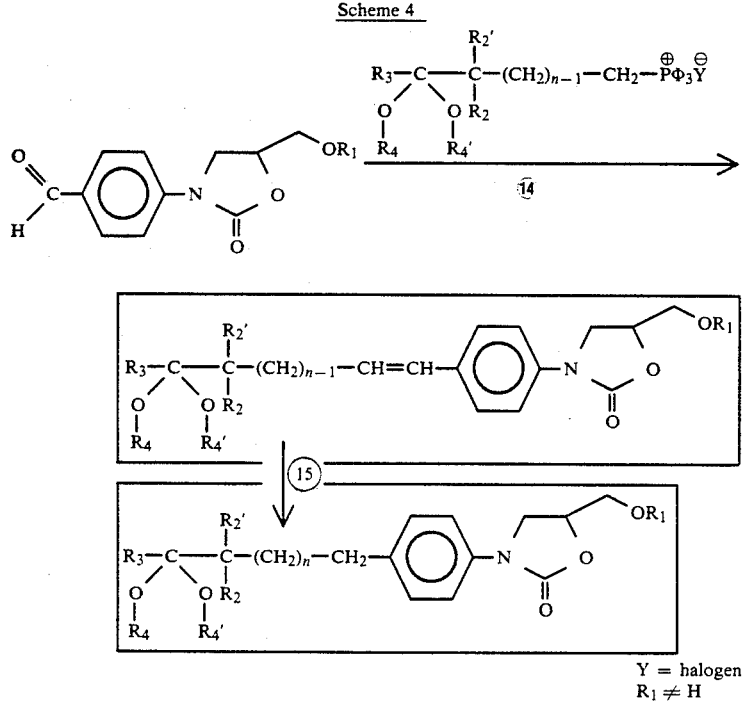
Y = halogen
$R_1 \neq H$
Scheme 5
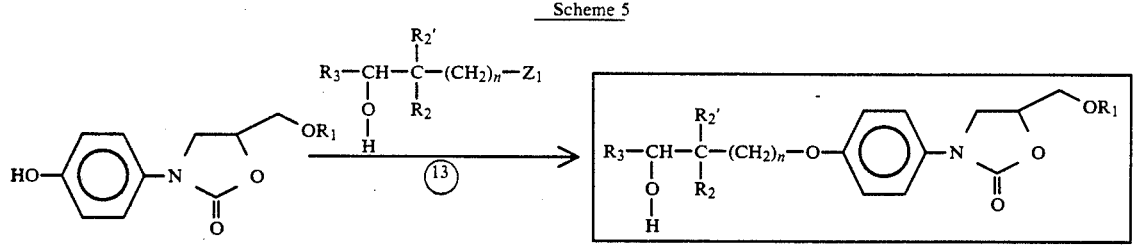
$R_2 = R_2' = H$
$Z_1$ is OTs, OMs or halogen
Scheme 6
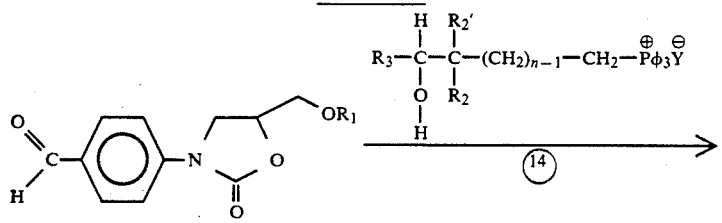

Scheme 6
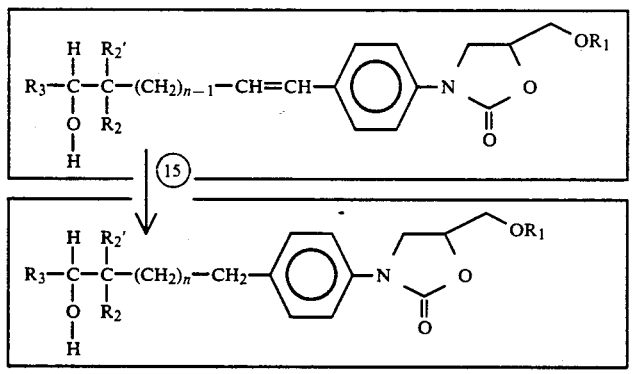
Y = halogen
R₁ ≠ H
Scheme 7
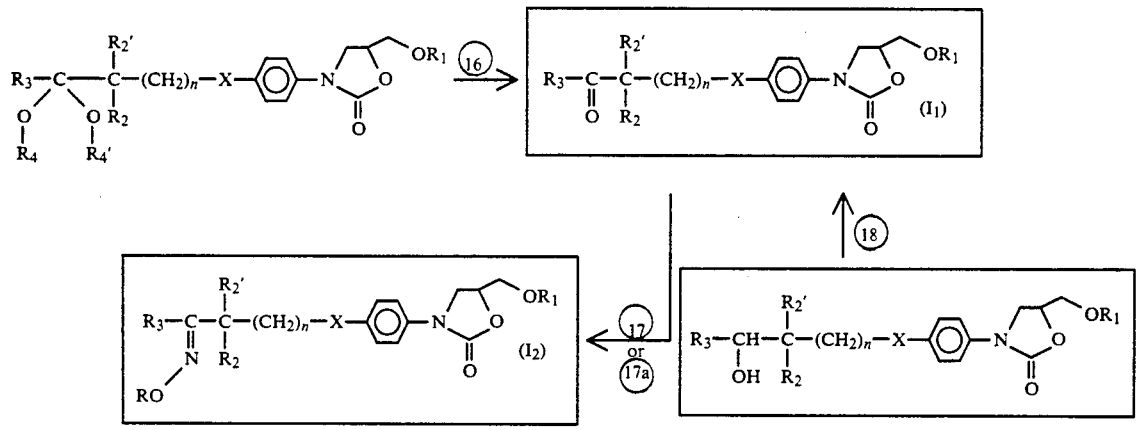
Scheme 8
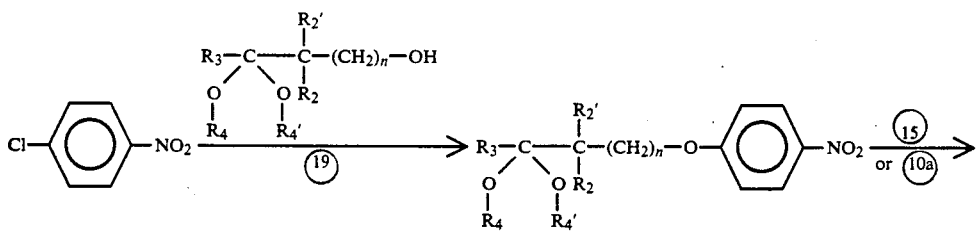
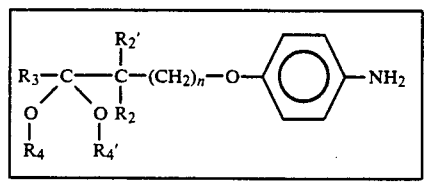
$(R_2, R_2') \neq (H, H)$ Scheme 9
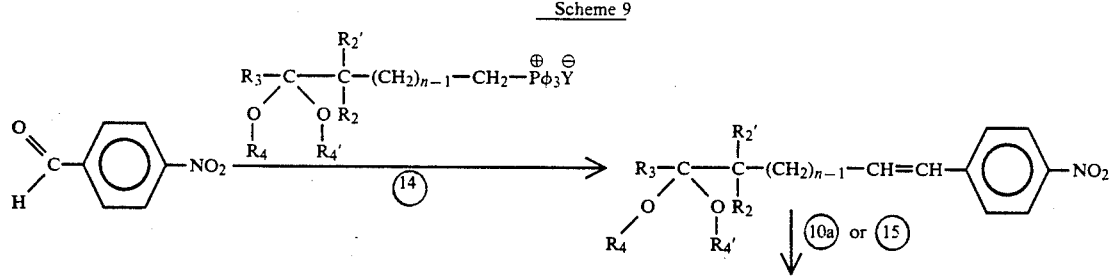
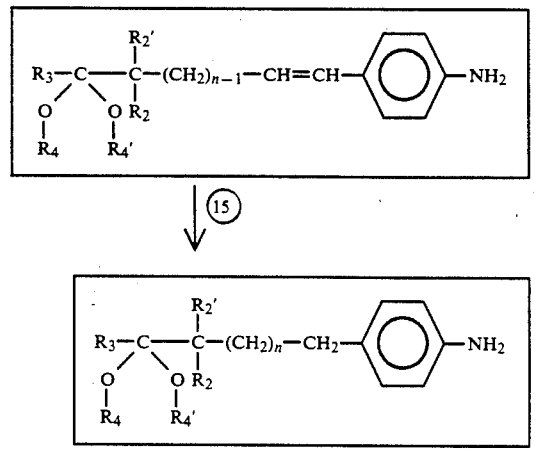
Y = Halogen
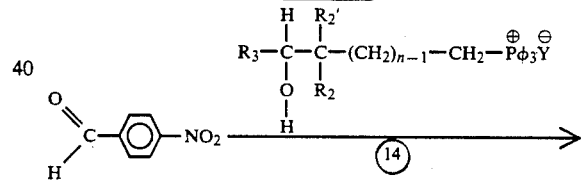
Scheme 10
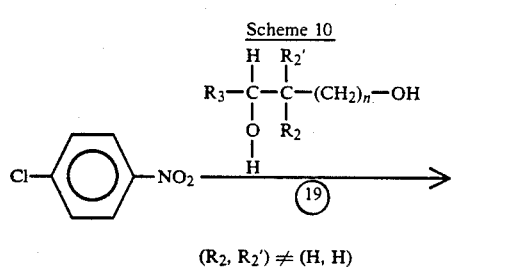
(R₂, R₂') ≠ (H, H)
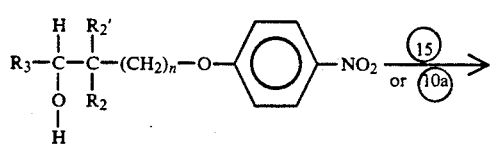
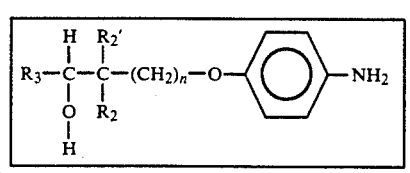
Scheme 11
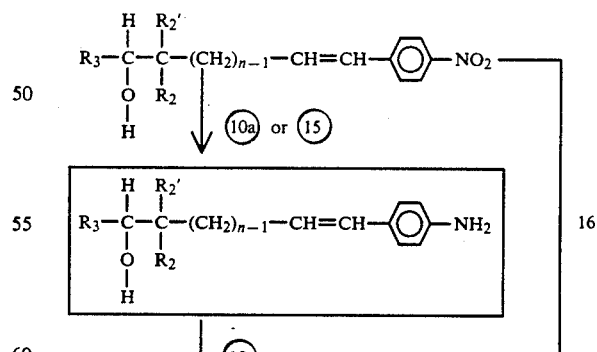
Y = Halogen
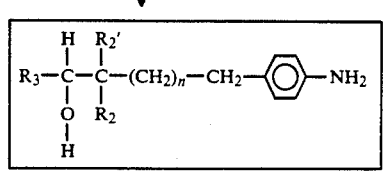

Scheme 12
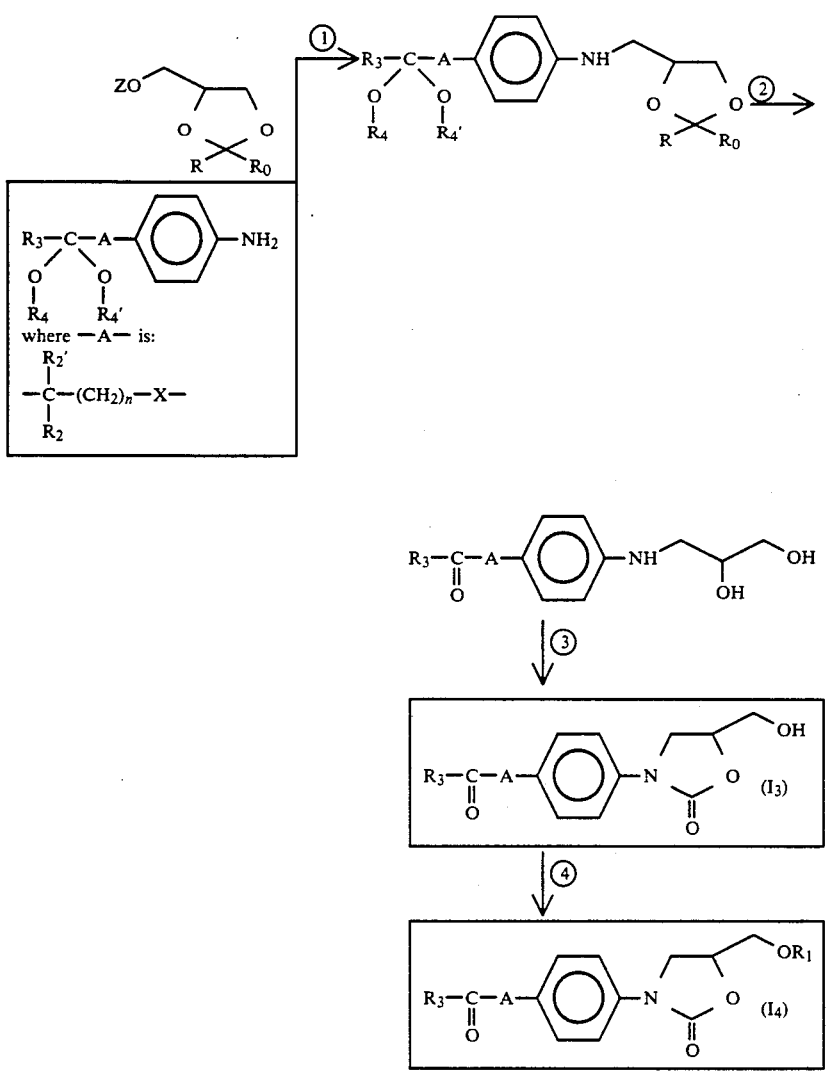
Z = Ts or Ms
$R_1 \neq H$
each of R and $R_0$ is $C_1$-$C_4$ alkyl or R and $R_0$ form together —$(CH_2)_5$—
Scheme 13
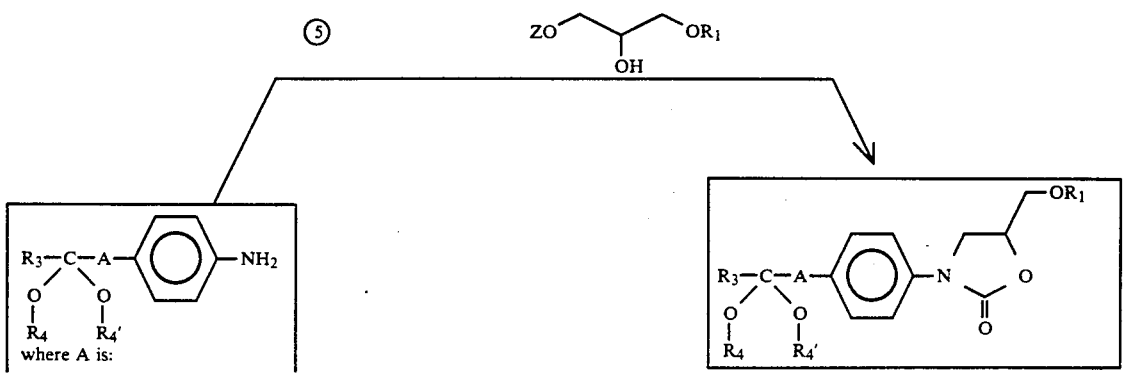

-continued
Scheme 13
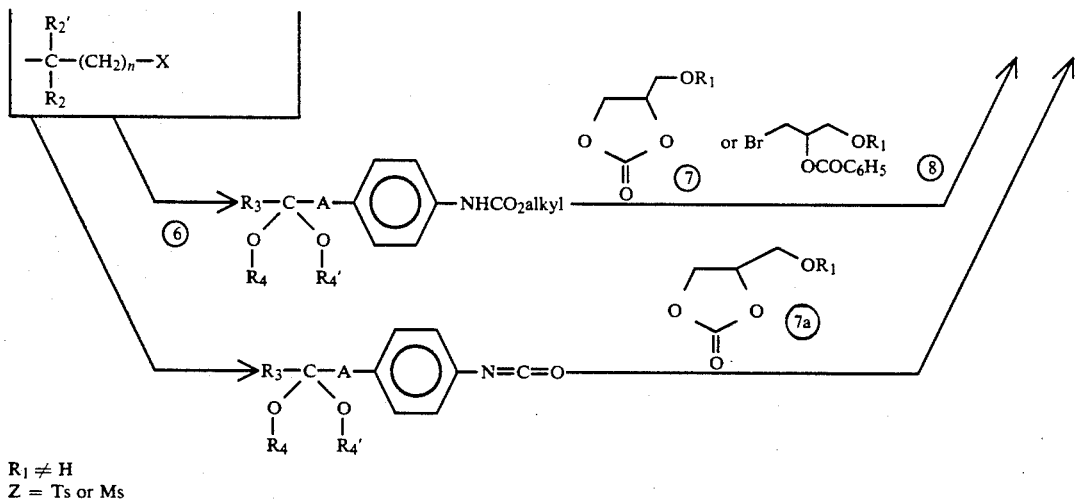
$R_1 \neq H$
$Z = Ts$ or $Ms$
Scheme 14
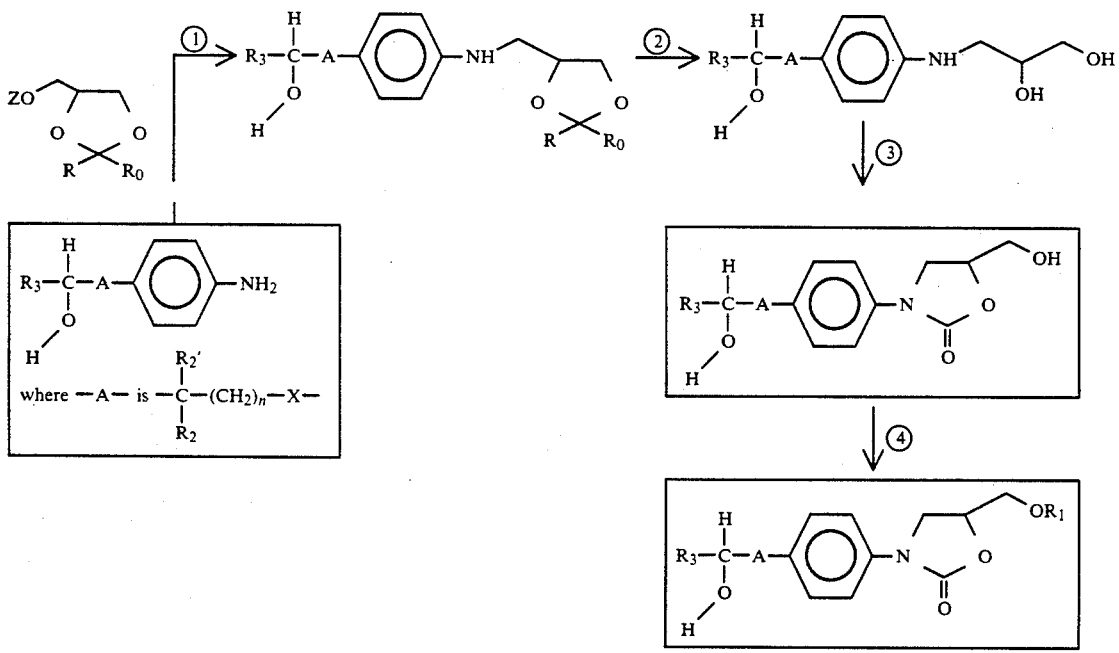
$Z = Ts$ or $Ms$
$R_1 \neq H$
each of $R$ and $R_0$ is $C_1$–$C_4$ alkyl or
$R$ and $R_0$ form together a —$(CH_2)_5$— chain
Moreover, the compounds of formulae:
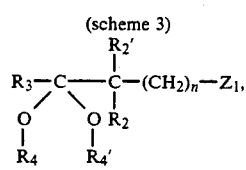
(scheme 3)
(schemes 4 and 9)
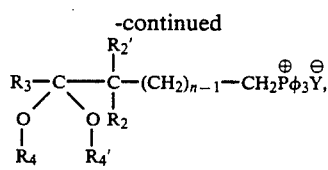
(scheme 8)
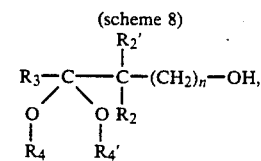

-continued (scheme 5)

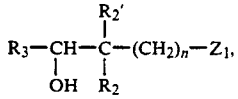

(schemes 6 and 11)

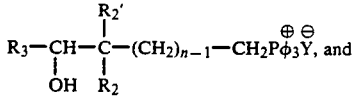

(scheme 10)

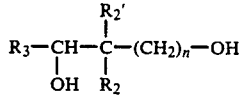

are obtained according to schemes 15 and 16.

④ Alkylation with a $C_1$–$C_4$ alkyl halogenide (bromide or chloride) in phase transfer conditions, particularly sodium hydroxide-methylene chloride or toluene, in the presence of a quaternary ammonium like tetrabutylammonium bromide or hydrogen sulphate.

⑤ Condensation in the presence of phosgene and a base, particularly dimethylaniline, in an organic solvent like methylene chloride, dichloroethane or toluene; and then ring formation by heating in an organic solvent particularly an alcoholic solvent like ethanol in the presence of a base, particularly potassium hydroxide.

⑥ Condensation with an alkyl chloroformate, like ethyl chloroformate, in the presence of a base, particularly, $NaHCO_3$, in a solvent mixture water-THF, at room temperature.

⑦ Condensation with heating (about 150° C.) in the presence of a base like $K_2CO_3$. The reaction retains the stereochemistry.

Scheme 15

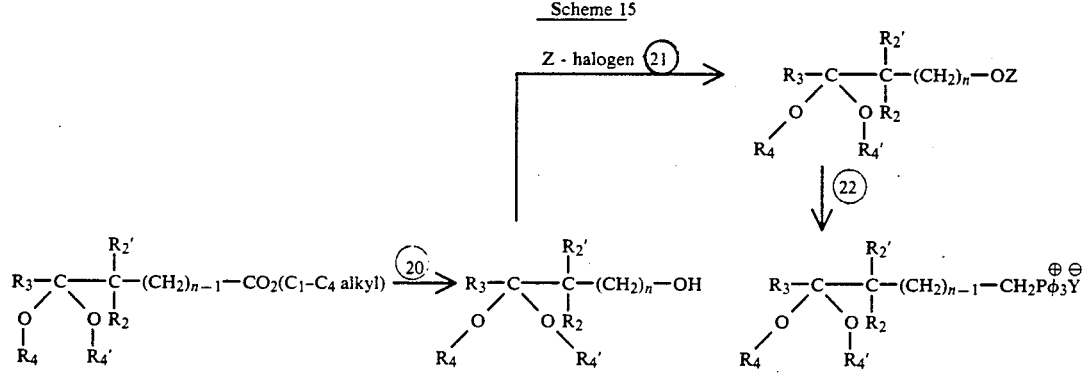

Z = Ts, Ms
Y = halogen

Scheme 16

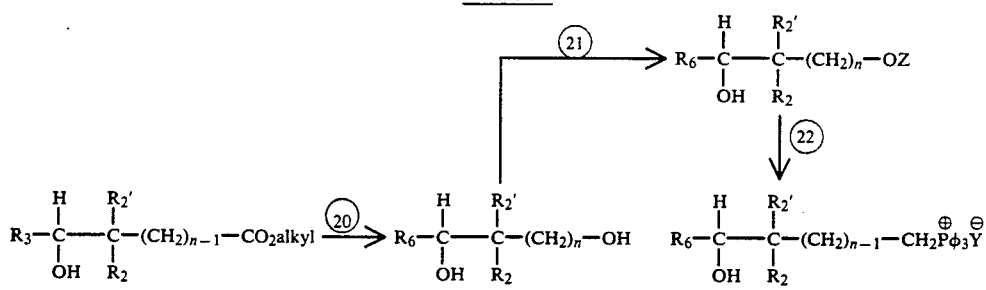

The ① to 22 numbers appearing in the above schemes have the following meanings:

① Condensation either in an anhydrous aprotic solvent like toluene, by heating, with or without a catalyst like hexadecyl tributyl phosphonium bromide or a quaternary ammonium halogenide such as benzyl triethylammonium bromide, or without a solvent in the presence of triethylamine between 130°–150° C.

② Hydrolysis with an aqueous acid, particularly 6N hydrochloric acid, in the presence of an organic solvent like methylethylketone. ③ Condensation with a $C_1$–$C_4$ alkyl carbonate, particularly, diethyl carbonate, in an anhydrous solvent like toluene in the presence of an alkali metal alkoxide like sodium methoxide.

7a Condensation in toluene in the presence of LiBr and $nBu_3PO$.

⑧ Condensation in the presence of a base, particularly NaH, in an aprotic solvent like THF, at 55° C.-60° C.

⑨ Debenzylation in an alcoholic solvent like methanol or ethanol, in the presence of hydrogen and a catalyst, particularly 10% palladium-carbon, humidified or not.

10 O-silylation of the alcohol in an aprotic organic solvent like THF or DMF, in the presence of a base, particularly imidazole, and of terbutyldimethylchlorosilane.

10a Reduction of the nitro derivative with powdered iron in the presence of ammonium chloride.

11 Hydrolysis in an organic solvent, particularly THF, in the presence of a fluoride, particularly tetrabutylammonium fluoride.

12 Oxidation in the presence of oxalyl chloride, DMSO and a base, particularly triethylamine, in an aprotic organic solvent like methylene chloride.

13 O-alkylation in an anhydrous organic solvent like methylethylketone or DMF, and in the presence of a base, particularly, $K_2CO_3$, or O-alkylation in an aprotic organic solvent like DMF and/or THF, and in the presence of an alkali metal hydride, like sodium hydride.

14 Condensation in the presence of a base particularly $K_2CO_3$, and of formamide in an organic solvent, particularly dioxane, preferably under reflux, or Condensation in the presence of LDA (lithium diisopropylamide) in a solvent mixture, particularly DMSO/THF.

15 Hydrogenation under atmospheric pressure of hydrogen in an organic solvent, particularly ethyl acetate, in the presence of a catalyst, like 10% palladium-carbon, humidified or not, or $PtO_2$ or Hydrogenation under hydrogen pressure, particularly, under 5 atm, in the presence of 10% palladium-carbon, humidified or not, or $PtO_2$, in an alcoholic solvent, particularly ethanol, or Hydrogenation under hydrogen pressure, particularly, under 9 atm, in the presence of 10% palladium-carbon, humidified or not, in an alcoholic solvent, particularly ethanol.

16 Hydrolysis preferably in the presence of silica and iron chloride hydrate in an organic solvent, particularly acetone or methylethylketone.

17 Condensation with a ($C_1$-$C_4$ alkoxy)amine or hydroxylamine salt, preferably in an alcoholic solvent (for example EtOH) and in the presence of a base (for example $NaHCO_3$)

17a Condensation with hydroxylamine in an alcoholic solvent, particularly ethanol.

18 Oxidation, for example with pyridinium dichromate, preferably in the presence of an acid like acetic acid, in an organic solvent like methylene chloride.

19 O-alkylation in an aprotic organic solvent, particularly DMF, in the presence of an alkali metal hydride, particularly sodium hydride.

20 Reduction in an aprotic organic solvent like dimethoxyethane, in the presence of lithium borohydride or in an organic solvent like THF in the presence of $LiAlH_4$.

21 Condensation in an organic solvent particularly pyridine or $CH_2Cl_2$, in the presence of a base, particularly 4-dimethylamino pyridine or $Et_3N$.

22 According to Helv. Chim. Acta 59, 755 (1976).

It should be moreover noted that, in the above schemes, each of $R_4$ and $R'_4$ independently is $C_1$-$C_4$ alkyl or $R_4$ and $R'_4$ form together a —$(CH_2)_2$— or —$(CH_2)_3$— chain.

The following preparations are given by way of examples for illustrating the invention.

EXAMPLE 1

Racemic mixture of diastereoisomers of 3-[4-(3-hydroxybutoxy)phenyl]-5-methoxymethyl-2-oxazolidinone (code number MD 370047)

To a solution of 27.5 g (0.112 mol) of 1-tosyloxy-3-butanol in 250 ml of methylethylketone, are added 28.2 g (0.2 mol) of $K_2CO_3$ and 22.8 g (0.102 mol) of 3-(4-hydroxyphenyl)-5-methoxymethyl-2-oxazolidinone (code number MD 780232). The mixture is heated under reflux for 4 h 30. After filtration and concentration, the residue is taken up in 200 ml of $CH_2Cl_2$, the organic phase is washed with NaCl saturated water, dried over $Na_2SO_4$ and concentrated. After purification by flash chromatography (silica, eluent: $CH_2Cl_2$: 98; $CH_3OH$: 2), the aimed product is obtained with a 70% yield, m.p.: 58° C.;

$^1H$ NMR ($CDCl_3$) δ ppm: 1.2 (3H); 1.8 (2H); 2.5 (1 exch. H); 3.4 (3H); 3.6 (2H); 3.7–4.2 (5H); 4.7 (1H); 6.8 (2H); 7.4 (2H);

IR (KBr) ν $cm^{-1}$: 3400, 1750, 1730.

EXAMPLE 2

3-[4-(3(R)-hydroxybutoxy)phenyl]-5(R)-methoxymethyl-2-oxazolidinone (code number 370120)

Step 1: 3-(4-benzyloxyphenyl)aminopropane-1,2-diol (R) (code number MD 200418)

In an autoclave 1.5 kg of 4-benzyloxyaniline (7.564 mol), 201.4 g of 1,4-dioxaspiro[4,5]decane-2-methanol (S)mesylate (8.048 mol) and 1.88 l of triethylamine (13.5 mol) are added. The reagents are heated at 140° C. for 30 min. The reaction medium is then taken up in 7 l of methylethylketone. The solution is washed with water and used for the subsequent step. To this solution, 1.2 l of 36% hydrochloric acid are added. The reaction medium is heated at 55° C. for 30 min. and cooled at 20° C. Soda lye is added until pH 9 is reached. The organic solution is washed with water and concentrated.

The product is obtained with a 90% yield; m.p.: 102° C.; $[α]_D^{20} = 12.7°$ (c=1, $CH_3OH$).

Step 2: 3-(4-benzyloxyphenyl) 5(R)-methoxymethyl-2-oxazolidinone (code number MD 200404)

a) To a suspension of 13 g (0.0475 mol) of compound MD 200418 in 100 ml of toluene, are added under reflux 6.2 ml (0.052 mol) of ethyl carbonate and 2 ml of 1M methanolic sodium methoxide. A distillation is carried out until the reflux reaches the boiling point of toluene. After cooling, $CH_2Cl_2$ is added and the organic solution is washed with water and dried over $Na_2SO_4$. After concentration, 14 g of 3-(4-benzyloxyphenyl)-5(R)-hydroxymethyl-2-oxazolidinone (code number MD 220201) are obtained:

m.p.: 157° C.; $[α]_D^{20} = -41°$ (c=1, $CH_2Cl_2$).

b) To 15 g (0.05 mol) of the previously obtained product (MD 220201), are added 100 ml of toluene and 18.9 g of methyl sulphate, 1.8 g of tetrabutylammonium hydrogen sulphate, 10 ml of water and 10 g of NaOH. The reagents are heated for ½ h. The reaction medium is extracted with isopropyl ether and the aimed product is obtained with a 83% yield;

m.p.: 101° C.; $[α]_D^{20} = -41.5°$ (c=1, $CH_2Cl_2$).

Using the same procedure but starting from the suitable reagents, there were obtained 3-(4-benzyloxy-phenyl)-5(S)-methoxymethyl-2-oxazolidinone (code number 340190):

m.p.: 101° C.; $[α]_D^{20} = +41.9°$ (c=1, $CH_2Cl_2$), as well as 3-(4-benzyloxyphenyl)-5(R)-ethoxymethyl-2-oxazolidinone (code number MD 230242):

m.p.: 78° C.; $[α]_D^{20} = -35.9°$ (c=1, $CH_2Cl_2$);

IR (KBr) ν $cm^{-1}$: 1750, 1735.

Step 3:
3-(4-hydroxyphenyl)-5(R)-methoxymethyl-2-oxazolidinone (code number MD 200405)

To a solution of 13 g (0.047 mol) of the compound MD 200404 in 80 ml of ethanol and 40 ml of $CH_2Cl_2$ in the presence of 2.6 g of 50% humidified 10% Pd/C, a hydrogen stream is passed through under normal pressure.

After completion of the reaction, the solution is filtered and concentrated. The aimed product is obtained with a 100% yield.

m.p.: 112° C.; $[\alpha]_D^{20} = -67°$ (c=1, $CH_3OH$);
IR (KBr) $\nu$ cm$^{-1}$: 3260, 1730.

Using the same process but starting from the corresponding reagents, there were obtained
the 3-(4-hydroxyphenyl)-5(S)-methoxymethyl-2-oxazolidinone derivative (code number MD 200717):
m.p.: 114° C.; $[\alpha]_D^{20} = +66°$ (c=1, $CH_3OH$),
as well as
the 3-(4-hydroxyphenyl)-5(R)-ethoxymethyl-2-oxazolidinone derivative (code number MD 230243):
m.p.: 92° C.; $[\alpha]_D^{20} = -58.9°$ (c=1, $CH_3OH$).
IR (KBr) $\nu$ cm$^{-1}$: 3300, 1770.

Step 4:
3-[4-(3(R)-hydroxybutoxy)phenyl]-5(R)-methoxymethyl-2-oxazolidinone (code number MD 370120)

To 100 ml of methylethylketone, are added 14.6 g (0.059 mol) of 1-tosyloxy-3-butanol (R) (Helv. Chim. Acta, 67, 89, 1984), 14.8 g (0.1 mol) of $K_2CO_3$ and 18 g (0.053 mol) of compound MD 200405. The mixture is heated under reflux 5 h after filtration, the reaction medium is concentrated, taken up in ethyl acetate, washed with water, dried over $Na_2SO_4$ and concentrated. The product is purified by flash chromatography (silica, eluent: $CH_2Cl_2$: 95; $CH_3OH$: 5);

m.p.: 76° C. $[\alpha]_D^{20}$: $-50.7°$ (c=1, $CH_2Cl_2$).

Using the same procedure, but reacting 1-tosylate-3-butanol (R) with compound MD 200717, there is obtained:
3-[4-(3(R)-hydroxybutoxy)phenyl]-5(S)-methoxymethyl-2-oxazolidinone (code number MD 370123):
m.p.: 44° C., $[\alpha]_D^{20}$: $+33°$ (c=1, $CH_2Cl_2$).

Likewise, there are obtained by reacting 1-tosyloxy-3-butanol (S) (J. Org. Chem. 47, 3850, 1982) with compound MD 200405
3-[4-(3-(S)-hydroxybutoxy)phenyl]-5(R)-methoxymethyl-2-oxazolidinone (code number MD 370122),
and with compound MD 200717,
3-[4-(3(S)-hydroxybutoxy)phenyl]-5(S)-methoxymethyl-2-oxazolidinone (code number MD 370121).

EXAMPLE 3
3-[4-[2-(2-methyl-1,3-dioxolane-2-yl)ethoxy]phenyl]-5(R)-methoxymethyl-2-oxazolidinone (code number MD 370296)

To a solution of 50 ml of DMF, are added 3 g (0.076 mol) of 60% NaH and, within 15 min., 16 g (0.076 mol) of the compound MD 200405 (Ex. 2, Step 3) dissolved in 75 ml of DMF. Then, while keeping temperature at 20° C., 0.836 mol of 2-(2-mesyloxyethyl)-2-methyldioxolane dissolved in 25 ml of DMF is added. The reaction medium is left at room temperature for 24 hours and poured on iced water. The aqueous phase is extracted with $CH_2Cl_2$ and the organic phase is dried over magnesium sulphate. The product is obtained after purification on silica column (eluent: Heptane: 40; Ethyl acetate: 60) with a 44% yield;

m.p. = 48° C.; $[\alpha]_D^{20} = -32.8°$ (c=1, $CH_2Cl_2$);
$^1$H NMR (CDCl$_3$) $\delta$ ppm: 1.4 (3H); 2.2 (2H); 3.4 (3H); 3,6 (2H); 3.9 (4H); 3.7–4,3 (4H); 4.7 (1H); 6.8 (2H); 7.4 (2H);
IR (KBr) $\nu$ cm$^{-1}$: 1740.
$^{13}$C NMR: Cq: 155.6; 154.4; 131.5; 108.7; CH: 120.2; 114.9; 71.2; CH$_2$: 72.7; 64.6; 64.3; 47.5; 38.2; CH$_3$: 59.6; 24.4.

In the same manner, there were obtained
3-[4-[3-(2-methyl-1,3 dioxolane-2-yl)propoxy]phenyl]-5(R)-methoxymethyl-2-oxazolidinone (code number MD 370506):
$^1$H NMR (CDCl$_3$) $\delta$ ppm: 1.35 (3H); 1.8 (4H); 3.4 (3H); 3.6 (2H); 3.7–4.2 (4H); 3.9 (4H); 4.7 (1H); 6.8 (2H); 7.4 (2H);
IR (KBr) $\nu$ cm$^{-1}$: 1750.
m.p. = 67° C.;

3-[4-[2-(2-methyl-1,3-dioxolane 2-yl)ethoxy]phenyl]-5(R)-hydroxymethyl-2-oxazolidinone (code number MD 230046):
$^1$H NMR (CDCl$_3$) $\delta$ ppm: 1.4 (3H); 2.15 (2H); 3 (1 exch. H); 3.9 (4H); 3.6–4.2 (6H); 4.6 (1H); 6.2 (2H); 7.4 (2H);
IR (KBr) $\nu$ cm$^{-1}$: 3480, 1710.
$[\alpha]_D^{20} = -40.2°$ (c=1, $CH_2Cl_2$);
m.p. = 132° C.
yield = 96%;

3-[4-(1,4-dioxaspiro[4,4]nonane[1,4]-6-yl-methoxy)-phenyl]-5(R)-methoxymethyl-2-oxazolidinone (code number MD 230204):
$[\alpha]_D^{20} = -44.8°$ (c=1, $CH_3OH$);
$^1$H NMR (CDCl$_3$) $\delta$ ppm: 1.4–2.6 (7H); 3.4 (3H); 3.6 (2H); 3.8–4.2 (8H); 4.7 (1H); 6.9 (2H); 7.4 (2H);
Oil.

EXAMPLE 4
3-[4-(3-oxobutoxy)phenyl]-5(R)-methoxymethyl-2-oxazolidinone (code number MD 370268)

Method 1

To a solution of 1.9 g (5.07×10$^{-3}$ mol) of pyridinium dichromate in 15 ml of methylene chloride, are added a drop of acetic acid and a molecular sieve 4 Å. And then a solution of 1 g of compound MD 370120 (Ex. 2) (3.38×10$^{-3}$ mol) in 5 ml of methylene chloride is added at 0° C. After 30 min. at 0° C., the mixture is let rise to room temperature and 5 g of cellite are added. After filtration and concentration, the residue is taken up in ethyl ether. The organic phase is concentrated and the precipitate is arranged in a mixture isopropyl ether-/ethyl ether (80/20). The aimed product is obtained with a 80% yield;

m.p.: 49° C.;
$[\alpha]_D^{20}$: $-42.6°$ (c=1, $CH_2Cl_2$);
$^1$H NMR (CDCl$_3$) $\delta$ ppm: 2.2 (3H); 2.85 (2H); 3.4 (3H); 3.6 (2H); 3.8–4.4 (4H); 4.7 (1H); 6.8 (2H); 7.4 (2H);
IR (KBr) $\nu$ cm$^{-1}$: 1750, 1710.

Method 2

To a solution of 294 g (0.871 mol) of compound MD 370296 (Example 3) in 2,5 l of acetone, are added 600 g of (FeCl$_3$, 6H$_2$O, SiO$_2$)$_n$ within 10 min. After 4 hours of stirring, the reaction medium is filtered and dried over Na$_2$SO$_4$ and concentrated. The product is obtained with a 74.1% yield, having the same characteristics as in Method 1

By one of the two methods previously described, there were also obtained:

3-[4-(4-oxopentoxy)phenyl]-5(R)-methoxymethyl-2-oxazolidinone (code number MD 370507)

$^1$H NMR (CDCl$_3$) δ ppm: 2 (2H); 2.15 (3H); 2.6 (2H); 3.4 (3H); 3.6 (2H); 3.9 (4H); 4.65 (1H); 6.8 (2H); 7.4 (2H);

IR (KBr) ν cm$^{-1}$: 1760, 1710;

[α]$_D^{20}$ = −40.3° (c=1, CH$_2$Cl$_2$);

m.p. = 70° C.

3-[4-(3-oxobutoxy)phenyl]-5(R)-hydroxymethyl-2-oxazolidinone (Method 1) (code number MD 230047)

$^1$H NMR (CDCl$_3$) δ ppm: 2.2 (3H); 2.9 (2H); 3.3-4.3 (4H); 4.2 (2H); 4.7 (1H); 5.2 (1 exch. H); 6.9 (2H); 7.5 (2H);

IR (KBr) ν cm$^{-1}$: 3450, 1720;

[α]$_D^{20}$ = −49.4° (c=1, CH$_3$OH);

m.p. = 126° C.

3-[4-(1-oxo-2-cyclopentylmethoxy)phenyl]-5(R)-methoxymethyl-2-oxazolidinone (code number MD 230200)

m.p.: 70° C.; [α]$_D^{20}$: −51.2° (c=1, CH$_3$OH);

$^1$H NMR (CDCl$_3$) δ ppm: 1.8-2.6 (7H); 3.4 (3H); 3.66 (2H); 3.8-4.2 (4H); 4.7 (1H); 6.9 (2H); 7.4 (2H).

EXAMPLE 5

3-[4-(3-N-hydroxyiminobutoxy)phenyl]-(R)-methoxymethyl-2-oxazolidinone (E and Z mixture) (code number MD 370298)

To a solution of 3.5 g (0.05 mol) of hydroxylamine hydrochloride and 4.2 g (0.05 mol) of sodium bicarbonate in 24 ml of water, is added a solution of 1.2 g (0.04 mol) of compound MD 370268 (Example 4) in 80 ml of ethanol. After 30 min. of stirring, the reaction medium is concentrated and taken up in a mixture of water and CH$_2$Cl$_2$. The organic phase is dried over Na$_2$SO$_4$ and concentrated. The product after recrystallization from ethanol is obtained with a 73% yield;

m.p.: 105° C.;

[α]$_D^{20}$: −40.3.° (c=1, CH$_2$Cl$_2$);

$^1$H NMR (DMSO d$_6$) δ ppm: 1.85 (3H); 2.7 (2H); 3.35 (3H); 3.6 (2H); 3.7-4.3 (4H); 4.8 (1H); 6.9 (2H); 7.4 (2H); 10.3 (1 exch. H);

IR (KBr) ν cm$^{-1}$: 3430, 1730.

In the same manner, there were obtained:

3-[4-(3-N-hydroxyiminobutoxy)phenyl]-5-methoxymethyl-2-oxazolidinone (code number MD 370307).

$^1$H NMR (DMSO d$_6$) δ ppm: 1.8 and 1.85 (3H); 2.7 (2H); 3.35 (3H); 3.6 (2H); 3.7-4.3 (4H); 4.8 (1H); 6.9 (2H); 7.4 (2H); 10.3 (1 exch. H);

IR (KBr) ν cm$^{-1}$: 3350, 1740;

3-[4-(3-N-methoxyiminobutoxy)phenyl]-5-methoxymethyl-2-oxazolidinone (code number MD 370326).

$^1$H NMR (CDCl$_3$) δ ppm: 1.85 and 1.90 (3H); 2.7 (2H); 3.4 (3H); 3.6 (2H); 3.8 (3H); 3.8-4.3 (4H); 4.7 (1H); 6.8 (2H); 7.4 (2H);

IR (microcell) ν cm$^{-1}$: 1750;

3-[4-(3-N-methoxyiminobutoxy)phenyl]-5(R)-methoxymethyl-2-oxazolidinone (code number MD 370299).

IR (microcell) ν cm$^{-1}$: 1760, 1730;

[α]$_D^{20}$: −39.4° (c=1, CH$_2$Cl$_2$);

$^1$H NMR (CDCl$_3$) δ ppm: 1.85 and 1.90 (3H); 2.7 (2H); 3.4 (3H); 3.6 (2H); 3.8 (3H); 3.7-4.3 (4H); 4.7 (1H); 6.8 (2H); 7.4 (2H);

3-[4-(4-N-hydroxyiminopentoxy)phenyl]-5(R)-methoxymethyl-2-oxazolidinone (code number MD 370508).

$^1$H NMR (CDCl$_3$) δ ppm: 1.9 (3H); 1.8-2.7 (4H); 3.4 (3H); 3.6 (2H); 3.7-4.2 (4H); 4.7 (1H); 6.9 (2H); 7.4 (2H); 9.1 (1 exch. H);

IR (KBr) ν cm$^{-1}$: 3460, 1740, 1720;

[α]$_D^{20}$: −39° (c=1, CH$_2$Cl$_2$); m.p.: 83° C.;

3-[4-(3-N-hydroxyiminobutoxy)phenyl]-5(R)-hydroxymethyl-2-oxazolidinone (code number MD 230001).

$^1$H NMR (DMSO d$_6$) δ ppm: 1.90 and 1.95 (3H); 2.7 (2H); 3.6-4.4 (6H); 4.8 (1H); 5.3 (1 exch. H); 7 (2H); 7.4 (2H); 10.5 (1 exch. H);

IR (KBr) ν cm$^{-1}$: 3450, 1730, 1700;

[α]$_D^{20}$ = −47.4° (c=1, CH$_3$OH); m.p.: 147.5° C.

EXAMPLE 6

3-[4-(3(E)-N-hydroxyiminobutoxy)phenyl]-5(R)-methoxymethyl-2-oxazolidinone(E) (code number MD 230050)

To a solution of 24 g (8.18.10$^{-2}$ mol) of compound MD 370268 (Example 4) in 240 ml of 96° ethanol, are added within 40 min. 9.1 g (0.13 mol) of hydroxylamine hydrochloride. After 1 h 30 of stirring, the aimed product is filtered and obtained with a 80% yield;

$^1$H NMR (CDCl$_3$) δ ppm: 1.8 (3H); 2.6 (2H); 3.3 (3H); 3.6 (2H); 3.6-4.4 (4H); 4.8 (1H); 6.9 (2H); 7.5 (2H); 10.2 (1 exch. H);

IR (KBr) ν cm$^{-1}$: 3420, 1730;

[α]$_D^{20}$: −41.4° (c=1, CH$_2$Cl$_2$); m.p.: 119° C.

EXAMPLE 7

3-[4-(3(Z)-N-hydroxyiminobutoxy)phenyl]-5(R)-methoxymethyl-2-oxazolidinone (code number MD 230062)

This compound was obtained by chromatography (silica, eluent: CH$_2$Cl$_2$: 97; isopropanol: 3) of the E and Z mixture MD 370298 (Example 5); m.p.: 114° C.;

$^1$H NMR (DMSO d$_6$) δ ppm: 1.85 (3H); 2.7 (2H); 3.3 (3H); 3.55 (2H); 3.6-4.25 (2H); 4.15 (1H); 4.6-5 (1H); 6.9 (2H); 7.5 (2H); 10.4 (1H);

IR (KBr) ν cm$^{-1}$: 3240, 1730.

EXAMPLE 8

3-[4-(3-oxo-2,2-dimethylbutoxy)phenyl]-5(R)-hydroxymethyl-2-oxazolidinone (code number MD 230109)

Step 1:

2,2-Dimethyl-2-(2-methyl-1,3-dioxolane-2-yl)ethanol (code number MD 230103)

A solution of 35 g (0.073 mol) of 2,2-dimethyl-2-(2-methyl-1,3-dioxolane-2-yl) acetic acid ethyl ester in 50 ml of THF is added at 0 C to a suspension of 7.23 g (0.19 mol) of LiAlH$_4$ in 300 ml of THF within 15 min. Then the reaction medium is hydrolyzed with 20 ml of water. After filtration and concentration, the product is obtained with a 92% yield.

IR (KBr) ν cm$^{-1}$: 3450, 2980, 2880;

$^1$H NMR (CDCl$_3$): 1 (6H); 1.2 (3H); 3.5 (2H); 4 (4H) [δ ppm]

Step 2:

2-methyl-2-[2-(4-nitrophenoxy)-1,1-dimethylethyl]-1,3-dioxolane (code number MD 230105)

To a solution of 1.6 g (0.01 mol) of compound MD 230103 in 13 ml of DMF, are added 0.48 g (0.01 mol) of 50% NaH. After 15 min. of stirring, a solution of 1.32 g (0.0084 mol) of parachloronitrobenzene is added and stirred at room temperature for 30 min.

The reaction medium is poured on water and extracted with isopropyl ether. The organic phases are washed with NaCl saturated water, dried over Na₂SO₄ and concentrated. The product is purified by flash chromatography (silica, eluent: heptane: 80; ethyl acetate: 20). Yield: 68%; oil;

¹H NMR (CDCl₃) δ ppm: 1.1 (6H); 1.3 (3H); 4 (6H); 6.9 (2H); 8.1 (2H).

Step 3:
2-methyl-2-[2-(4-aminophenoxy)-1,1-dimethylethyl]-1,3-dioxolane (code number MD 230106)

To a solution of 18.4 g (65.4×10⁻³ mol) of compound 230105 in 180 ml of ethanol in the presence of 50% humidified 10% Pd/C, a hydrogen stream is passed through under normal pressure for 3 h 30. After filtration and concentration, the product is purified by flash chromatography (silica, eluent: ethyl acetate: 30; heptane: 70):

¹H NMR (CDCl₃) δ ppm: 1.05 (6H); 1.3 (3H); 3.3 (2 exch. H); 3.7 (2H); 3.9 (4H); 6.7 (4H).
IR (microcell) ν cm⁻¹: 3460, 3450.

Step 4:
N-[4-[2-(2-methyl-1,3-dioxolane-2-yl)-1,1-dimethylethoxy]phenyl]-1,4-dioxaspiro[4,5]decane-2-methanamine (R) (code number MD230107)

8.8 g (0.035 mol) of compound MD 230106; 12.6 g (0.036 mol) of 1,4-dioxaspiro[4.5]decane-2-methanol (S) tosylate and 5.4 g (0.054 mol) of triethylamine are heated in a bomb at 130° C.-140° C. for 2 h. After cooling, the reaction mixture is taken up in ethyl acetate. The organic phase is washed with NaCl saturated water and concentrated. The product is obtained after chromatography (silica, eluent: heptane 80 - ethyl acetate 20). Yield: 63%.

¹H NMR (CDCl₃) δ ppm: 1.1 (6H); 1.35 (3H); 1.6 (10H); 3.2 (2H); 3.6-4.5 (10 H of which 1 exch.); 6.65 (4H).
IR (microcell) ν cm⁻¹: 3400.
[α]$_D^{20}$ = −1.2° (c =1, MeOH).

Step 5:
3-[4-(3-oxo-2,2-dimethylbutoxy)phenyl]aminopropane-1,2 -diol (R) (code number MD 230108)

To a solution of 0.7 g (1.7×10⁻³ mol) of compound MD 230107 in 3.5 ml of THF, are dropwise added 3.5 ml of 6N hydrochloric acid. After 1 h, the reaction medium is poured on water and extracted with ethyl acetate. The organic phase is washed with water, dried over Na₂SO₄ and concentrated. 80% yield.
IR (microcell) ν cm⁻¹: 3400, 1710.

Step 6:
3-[4-(3-oxo-2,2-dimethylbutoxy)phenyl]-5(R)-hydroxymethyl-2-oxazolidinone (code number MD 230109)

A solution of 3.9 g (0.0139 mol) of compound MD 230108 in 50 ml of toluene is heated under reflux and 1.88 g (0.0159 mol) of diethyl carbonate are added at 90° C., and then gradually 0.32 ml of a 4.3 mol/liter sodium methoxide solution.

After distilling off the alcohol, the reaction mixture is concentrated. The residue is taken up in ethyl acetate. The organic phase is washed with water, dried and concentrated. The product is obtained after column chromatography (silica, eluent: CH₂Cl₂);
m.p.=109° C.;
[α]$_D^{20}$= −44.4° (c=1, MeOH);

¹H NMR (CDCl₃) δ ppm: 1.25 (6H); 2.2 (3H); 3.9 (6H); 4.7 (1H); 6.9 (2H); 7.4 (2H);
IR (KBr) ν cm⁻¹: 3450, 1745-1725.

EXAMPLE 9

3-[4-(3-oxo-2,2-dimethylbutoxy)phenyl]-5(R)-methoxymethyl-2-oxazolidinone (code number 230073)

To a suspension of 2.9 g (0.009 mol) of compound MD230109 in 40 ml of toluene, are added 3.8 g of 50% sodium hydroxide, 0.3 g of tetrabutylammonium bromide and 3,6 g (0,0293 mol) of methyl sulphate. After 10 min. of stirring, the reaction medium is poured on water. The organic phase is washed with water, dried over Na₂SO₄ and concentrated, and the product is obtained after chromatography (silica, eluent: ethyl acetate: 50; heptane: 50).
m.p.: 75° C.; [α]$_D^{20}$: −52° (c=1, MeOH);

¹H NMR (CDCl₃) δ ppm: 1.25 (6H); 2.2 (3H); 3.6 (2H); 3.7-4.2 (2H); 3.9 (2H); 4.65 (1H); 6.8 (2H); 7.4 (2H);
¹³C NMR (CDCl₃) δ ppm: Cq: 211.9; 155.8; 154.9; 132; 48.4; CH: 120.3; 115.1; 71.3; CH₂: 74.9; 72.8; 47.8; CH₃: 25.8; 22;
IR (KBr) ν cm⁻¹: 1735, 1715.

EXAMPLE 10

3-[4-(4-oxopentyl)phenyl]-5(R)-hydroxymethyl-2-oxazolidinone (code number MD230116)

Step 1: 2-(p-nitrocinnamyl)-2-methyl-1,3-dioxolane (code number MD230111)

To 62.8 mmol of LDA in 226.4 ml of THF, is added dropwise at 0° C. a solution of 28.8 g (62.2 mmol) of (2-methyl-dioxolane-2-yl-2-ethyl)triphenylphosphonium bromide in 60 ml of DMSO. After 1 h at 0° C., 7.8 g (51.6 mmol) of p-nitrobenzaldehyde dissolved in 40 ml of THF are added. The reaction medium is hydrolyzed with a NH₄Cl saturated solution and is extracted with ethyl ether. The organic phase is dried over Na₂SO₄ and concentrated. After purification by flash chromatography (silica, eluent: heptane: 70; ethyl acetate: 30), the product is obtained with a 48% yield.

¹H NMR (CDCl₃) δ ppm: 1.3 (3H); 2.6 (2H); 4 (4H); 5.7-6.5 (2H); 7.4 (2H); 8.1 (2H).

Step 2: 2-(4-aminocinnamyl)-2-methyl-1,3-dioxolane (code number MD230112)

A solution of 8 g (32 mmol) of compound MD230111 in 100 ml of ethanol in the presence of 0.8 g of 10% Pd/C in an autoclave, is hydrogenated under 5 atm for 4 h. After filtration, concentration, purification by flash chromatography (silica, eluent: heptane: 50; ethyl acetate: 50), the product is obtained with a 89% yield.
m.p.: <50° C.;

¹H NMR (CDCl₃) δ ppm: 1.35 (3H); 2.4-2.8 (2H); 3.6 (2exch. H); 4 (4H); 5.5-6.3 (2H); 6.6 (2H); 7.2 (2H);
IR (microcell) ν cm⁻¹: 3460, 3440.

Step 3:
2-(4-aminophenylpropyl)-2-methyl-1,3-dioxolane (code number MD230113)

A solution of 15.4 g (70.23 mmol) of compound MD230112 in 100 ml of ethanol in the presence of 1.5 g of 10% Pd/C in an autoclave is hydrogenated under 9 atm for 1 h. After filtration and concentration, 15.5 g of the aimed product (liquid) are obtained.

¹H NMR (CDCl₃) δ ppm: 1.25 (3H); 1.6 (4H); 2.45 (2H); 3.5 (2 exch. H); 3.85 (4H); 6.55 (2H); 6.9 (2H).
IR (microcell , ν cm⁻¹): 3460, 3350.

Step 4:
[4-[3-(2-methyl-1,3-dioxolane-2-yl)propyl]phenyl]-1,4-dioxaspiro[4,5]decane-2-methanamine (R) (code number MD230114)

To a mixture of 1 g (4.5 mmol) of compound MD230113 and 1.62 g (4.97 mmol) of 1,4-dioxaspiro[4.5]decane-2-methanol (S)tosylate, is added 0.73 g (1 ml, 7.23 mmol) of triethylamine and the mixture is heated at 140° C. for 5 h. The reaction medium is taken up in water and extracted with ethyl acetate. The organic phase is washed with salted water, and then dried over Na₂SO₄. The product as a liquid is obtained with a 59% yield after flash chromatography (silica, eluent: heptane: 40; ethyl acetate: 60).

¹H NMR (CDCl₃) δ ppm: 1.2 (3H); 1.5 (10H); 1.6 (4H); 2.4 (3H); 3.15 (3H); 3.8 (4H); 3.6–4.5 (3H).
IR (microcell) ν cm⁻¹: 3400;
$[\alpha]_D^{20} = -2.9°$ (c=1, MeOH).

Step 5: [4-(4-oxopentyl)phenyl]aminopropane-1,2-diol (R) (code number MD230115)

This compound was obtained according to the same procedure as that of Step 5 of Example 8
¹H NMR (CDCl₃) δ ppm: 1.8 (2H); 2 (3H); 2.4 (4H); 2.7-3.3 (3H); 3.1 (3H); 3.6 (2H); 3.3 (1H); 6.5 (2H); 6.9 (2H).

Step 6:
3-[4-(4-oxopentyl)phenyl]-5(R)-hydroxymethyl-2-oxazolidinone (code number MD230116)

This compound was obtained according to the same procedure as that of the Step 6 of Example 8:
m.p.=110° C.;
$[\alpha]_D^{20} = -50.7°$ (c=1, MeOH);
¹H NMR (CDCl₃) δ ppm: 1.8 (2H); 2.05 (3H); 2.2-2.7 (4H); 2.75 (1H); 3.65-4.10 (2H); 4.65 (1H); 7.1 (2H); 7.4 (2H);
IR (KBr) ν cm⁻¹: 3460, 1720.

EXAMPLE 11
3-[4-(4-oxopentyl)phenyl]-5(R)-methoxymethyl-2-oxazolidinone (code number MD230083)

This compound was obtained with a 100% yield according to the same procedure as that of Example 9, from the compound obtained in Step 6 of Example 10:
m.p.: <50° C.;
$[\alpha]_D^{20} = -56.9°$ (c=1, MeOH);
¹H NMR (CDCl₃) δ ppm: 1.9 (2H); 2.1 (3H); 2.45 (4H); 3.4 (3H); 3.6 (2H); 3.9 (2H); 4.7 (1H); 7.1 (2H); 7.4 (2H);
IR (KBr) ν cm⁻¹: 1750, 1710.

EXAMPLE 12
3-[4-(4(R)-hydroxypentyl)phenyl]-5(R)-methoxymethyl-2-oxazolidinone (code number MD 230238)

Step 1: 4-Terbutyl dimethyl silyloxy methyl-1-nitro-benzene (code number MD 230245)

To a solution of 465.4 g (3.039 mol) of paranitrobenzyl alcohol in 2.5 l of DMF, are added 310 g (4.559 mol) of imidazole, and then 504 g (3.347 mol) of terbutyl dimethylchlorosilane. After 1 h of stirring at room temperature, the reaction medium is poured on water. The aqueous phase is extracted with methylene chloride. The organic phase is dried over Na₂SO₄ and concentrated: oil;
¹H NMR (CDCl₃) δ ppm: 0.2 (6H); 1 (9H); 4.9 (2H); 7.6 (2H); 8.2 (2H);
IR (microcell) ν cm⁻¹: 1520, 1340, 1030, 840.

Step 2: 4-Terbutyl dimethyl silyloxy methyl aniline (code number MD 230246)

To 772 ml of 0.1N ammonium chloride, are added 77.2 g (0.288 mol) of the previously obtained compound MD 230245 and 120.9 g of powdered iron and the mixture is heated under reflux for 2 h. After cooling, 20 ml of concentrated ammonia are added, the reaction medium is filtered and extracted with toluene. The organic phase is washed with water, dried over Na₂SO₄ and concentrated.
b.p.₀.₀₁ mm Hg:88°-93° C.;
¹H NMR (CDCl₃) δ ppm: 0.2 (6H); 1.05 (9H); 3.6 (2H); 4.8 (2H); 6.75 (2H); 7.2 (2H);
IR (microcell) ν cm⁻¹: 3450, 3350.

Step 3: 3-[4-(terbutyl dimethyl silyloxy methyl)phenyl]-5(R)-methoxymethyl-2-oxazolidinone (code number MD 230247)

To a solution of 43.8 g (0.168 mol) of 3-methoxy-propane-1,2-diol (R) tosylate in 200 ml of toluene, are added 130 ml of a 1.93 molar toluene solution of phosgene, and then dropwise 37.8 g (0.252 mol) of diethylaniline. After cooling, iced water is added and the organic phase is decanted and dried over Na₂SO₄. This solution is then added to a solution of 40 g (0.168 mol) of compound MD 230246 (Step 2) and of 20.5 g (0.168 mol) of 4-dimethylaminopyridine in 600 ml of toluene. After ½ h of stirring, the reaction medium is poured on water and the organic phase is washed with a solution of sodium bicarbonate, and then with a NaCl saturated solution. After concentration, the resulting product (84.5 g) is dissolved in 800 ml of ethanol to which are added 12.2 g (0.218 mol) of KOH as tablets. After ½ h of stirring, the reaction medium is poured on water and extracted with methylene chloride. The organic phase is dried over Na₂SO₄ and concentrated. The aimed product is obtained after chromatography (silica, eluent: ethyl acetate 30, heptane 70) with a 63% yield.
$[\alpha]_D^{20} = -46.2°$ (c=1, CH₃OH);
IR (KBr) ν cm⁻¹: 1755, 1735;
¹H NMR (CDCl₃) δ ppm: 0 (6H); 1 (9H); 3.4 (3H); 3.6 (2H); 3.8-4.2 (2H); 4.7 (3H); 7.5 (4H);
m.p. <50° C.

Step 4:
3-[4-(hydroxymethyl)phenyl]-5(R)-methoxymethyl-2-oxazolidinone (code number MD 230248)

A solution of 29.2 g (0.083 mol) of compound MD 230247 and 7.8 g (0.025 mol) of teterabutylammonium fluoride trihydrate in 200 ml of THF is stirred for 12 h at room temperature and concentrated. The product is obtained after chromatography (silica, eluent: ethyl acetate 50, heptane 50);
m.p.=65° C.;
IR (KBr) ν cm⁻¹: 3400, 1750, 1720,
¹H NMR (CDCl₃) δ ppm: 2.4 (1 exch. H); 3.35 (3H); 3.6 (2H); 3.8-4.2 (2H); 4.6 (2H); 7.35 (4H).

Step 5:
3-(4-carboxaldehydophenyl)-5(R)-methoxymethyl-2-oxazolidinone (code number MD 230256)

To a solution cooled at −60° C. of 12.46 g (0.0982 mol) of oxalyl chloride in 80 ml of methylene chloride, is added within 20 min. a solution of 12.76 g (0.1630 mol) of DMSO in 80 ml of methylene chloride. After 40 min., a solution of 19.6 g (0.0818 mol) of compound MD 230248 in 80 ml of methylene chloride is added, and then 1.4 g (0.409 mol) of triethylamine. After return to room temperature, 300 ml of water are added. The organic phase is washed with water, dried and concentrated. The product was obtained after purification by chromatography (silica, eluent: ethyl acetate 70, heptane 30) with a 80% yield;

m.p.=96° C.;
$[\alpha]_D^{20}= -73.4°$ (c=1, $CH_2Cl_2$);
IR (KBr) $\nu$ cm$^{-1}$: 1740, 1690;
$^1$H NMR (CDCl$_3$) $\delta$ ppm: 3.4 (3H); 3.7 (2H); 3.8–4.3 (2H); 4.8 (1H); 7.8 (4H); 9.8 (1H).

Step 6:
3-[4-(4(R)-hydroxypentyl)phenyl]-5(R)-methoxymethyl-2-oxazolidinone (code number MD 230238)

A solution of 3.3 g (0.00712 mol) of 2(R)-hydroxypropyltriphenylphosphonium iodide (Helv. Chim. Acta, 59, 755–757, 1976), 1.34 q (0.00569 mol) of compound MD 230256 and 2.9 g (0.0213 mol) of $K_2CO_3$ in 10 ml of dioxane and 1.5 ml of formamide is heated under reflux for 20 h. After filtration and concentration, the resulting insaturated product is purified by dissolving it in 30 ml of DMF, and 0.58 g of imidazole and 0.94 g (0.00625 mol) of terbutyl dimethylchlorosilane are added. After 24 hours of stirring, the reaction medium is poured on water. The silylated product is extracted with methylene chloride and purified by chromatography (silica, eluent: ethyl acetate: 50 heptane: 50) with a 36% yield. 0.84 g of the resulting product is dissolved in 15 ml of THF in the presence of 0.65 g of tetrabutylammonium fluoride for 12 h. After concentration and purification by chromatography (silica, eluent: ethyl acetate: 70, heptane: 30), 0.53 g (0.0018 mol) of the purified insaturated product dissolved in 10 ml of methanol in the presence of (50% humidified) 10% palladium-carbon is hydrogenated under normal pressure. The aimed product is obtained with a 55% yield after chromatography (silica, ethyl acetate: 60, heptane: 40), $[\alpha]_D^{20}= -45.8°$ (c=1, $CH_2Cl_2$);
IR (KBr) $\nu$ cm$^{-1}$: 3400, 1735;
m.p.: 47° C.;
$^1$H NMR (CDCl$_3$) $\delta$ ppm: 1.2 (3H); 1.5 (4H); 1.8 (1 exch. H); 2.6 (2H); 3.4 (3H); 3.6 (2H); 3.7–4.2 (3H); 4.7 (1H); 7.2 (2H); 7.4 (2H).

In the same manner, there was obtained:
3-[4-(4(S)-hydroxypentyl)phenyl]-5(R)-methoxymethyl-2-oxazolidinone (code number MD 230239);
m.p.: 53° C.; $[\alpha]_D^{20}$: −35.9° (c=1, $CH_2Cl_2$);
IR (KBr) $\nu$ cm$^{-1}$: 3400, 1740;
$^1$H NMR (CDCl$_3$) $\delta$ ppm: 1.1 (3H); 1.6 (5H of which 1 exch.); 3.4 (3H); 3.6 (2H); 3.7–4.2 (3H); 4.7 (1H); 7.1 (2H); 7.4 (2H).

EXAMPLE 13

3-[4-[3-(2-phenylmethyl-1,3-dioxolane-2-yl)propyl]-phenyl]-5(R)-methoxymethyl-2-oxazolidinone (code number MD 360334)

Step 1: 2-[2-(phenylmethyl)-1,3-dioxolane-2-yl]ethanol (code number MD 360370)

This compound is obtained according to the method described in Step 1 of Example 8, from [2-(phenylmethyl)-1,3-dioxolane-2-yl]acetic acid ethyl ester (Synthesis 451, 1982):
IR (microcell) $\nu$ cm$^{-1}$: 3440–3400;
$^1$H NMR (CDCl$_3$) $\delta$ ppm: 1.9 (2H); 2.8 (3H of which 1 exch.); 3.5–4 (6H); 7.2 (5H);

Step 2:
2-(phenylmethyl)-2-(2-bromoethyl)-1,3-dioxolane (code number MD 360371)

To a solution of 37.8 g (0.181 mol) of compound 360370 in 200 ml of $CH_2Cl_2$, are added 120.4 g (0.363 mol) of $CBr_4$, and then gradually 95.2 g (0.363 mol) of triphenylphosphine, and then the reaction medium is stirred at room temperature for ½ hour. After filtration, the organic phase is concentrated. Yield: 81%;
IR (microcell) $\nu$ cm$^{-1}$: 3020, 2960, 2880, 1605;
$^1$H NMR (CDCl$_3$) $\delta$ ppm: 2.2 (2H); 2.8 (2H); 3.4 (2H); 3.8 (4H); 7.2 (5H).

Step 3: [2-(phenylmethyl)-1,3-dioxolane 2-yl]ethyl]triphenylphosphonium bromide (code number M 360372)

To a solution of 33 g (0.1217 mol) of compound 360371 in 200 ml of dioxane, are added 31 g (0.1217 mol) of triphenylphosphine and the mixture is heated for 20 hours. After cooling, the precipitate is filtered and washed with dioxane and ethyl ether. Yield: 81%;
m.p.=225° C.;
$^1$H NMR (CDCl$_3$) $\delta$ ppm: 1.6–2.2 (2H); 3 (2H); 3.2–4.2 (6H); 7.2 (5H); 7.5–7.9 (15H).

In the same manner, there were obtained
[2-(2-phenyl-1,3-dioxolane-2-yl)ethyl]triphenylphosphonium bromide
m.p.: 228° C.;
1H NMR (CDCl$_3$) $\delta$ ppm: 2–2.5 (2H); 3.4–4.4 (6H); 7.4 (5H); 7.6–8 (15H)
from 2-phenyl-2-(2-bromoethyl)-1,3-dioxolane (Tetrahedron Letters, 1987, 28, 1397).
[2-(2-cyclohexyl-1,3-dioxolane-2-yl)ethyl]triphenylphosphonium bromide from 2-cyclohexyl-2-(2-bromoethyl)-1,3-dioxolane: Liq.,
IR (microcell) $\nu$ cm$^{-1}$: 2920–2850, 1440–1110;
$^1$H NMR (CDCl$_3$) $\delta$ ppm: 0.9–2.3 (13H); 3–4.2 (6H); 7.6–8 (15H).

Step 4:
2-(Para-nitrocinnamyl)-2-(phenylmethyl)-1,3-dioxolane (code number MD 360373)

This compound is obtained according to the procedure of Step 1 of Example 10: liquid;
IR (microcell) $\nu$ cm$^{-1}$: 1595, 1510, 1340;
$^1$H NMR (CDCl$_3$) $\delta$ ppm: 2.6 (2H); 3 (2H); 3.9 (4H); 5.8–6.8 (2H); 7.3 (5H); 7.4 (2H); 8.2 (2H).

In the same manner, there were obtained:
2-(para-nitrocinnamyl)-2-phenyl-1,3-dioxolane (code number MD 360384)
IR (microcell) $\nu$ cm$^{-1}$: 1595, 1510, 1340, ¹H NMR (CDCl₃) δ ppm: 2.8–3 (2H); 3.6–4.2 (4H); 5.6–6.8 (2H); 7.15–7.65 (7H); 8.1 (2H);
m.p.=82° C.;
2-(para-nitrocinnamyl)-2-cyclohexyl-1,3-dioxolane (code number MD 360416)
IR (microcell) $\nu$ cm⁻¹: 2920–2850, 1595–1510, 1390,
¹H NMR (CDCl₃) δ ppm: 0.8–2.1 (11H); 2.5–2.8 (2H); 4 (4H); 5.7–6.7 (2H); 7.45 (3H); 8.2 (2H).

Step 5:
2-[3-(4-aminophenyl)propyl]-2-(phenylmethyl)-3-dioxolane (code number MD 360374)

This compound is obtained by hydrogenating compound MD 360373 according to the procedure of Step 3 of Example 10.
m.p.=55° C.;
IR (KBr) $\nu$ cm⁻¹: 3450–3360, 1620–1510;
¹H NMR (CDCl₃) δ ppm: 1.65 (4H); 2.45 (2H); 2.85 (2H); 3.45 (2 exch. H); 3.45–4 (4H); 6.5 (2H); 6.9 (2H); 7.2 (5H).
In the same manner, there were obtained:
2-[3-(4-aminophenyl)propyl]-2-phenyl-1,3-dioxolane (code number MD 360385)
m.p.=68° C.;
IR=(KBr) $\nu$ cm⁻¹: 3440–3360, 1630–1610, 1515;
¹H NMR (CDCl₃) δ ppm: 1.4–2.2 (4H); 2.4 (2H); 3.45 (2H); 3.6–4.15 (4H); 6.5 (2H); 6.9 (2H); 7.2–7.6 (5H);
2-[3-(4-aminophenyl)propyl]-2-cyclohexyl-1,3-dioxolane (code number MD 360417)
IR (microcell) $\nu$ cm⁻¹: 3440–3360, 1625;
¹H NMR (CDCl₃) δ ppm: 0.8–2 (11H); 2.4 (2H); 3.45 (2 exch. H); 3.8 (4H); 6.5 (2H); 6.9 (2H).

Step 6:
2-[3-[4-(ethoxycarbonylamino)phenyl]propyl]-2-(phenylmethyl)-1,3-dioxolane (code number MD 360375)

This compound is obtained by reacting ethyl chloroformate (55.10⁻³ mol) with a solution of compound MD 360374 (10⁻³ mol) dissolved in a mixture THF/water (90/10) in the presence of sodium bicarbonate (6.3 g).
¹H NMR (CDCl₃) δ ppm: 1.25 (3H); 1.65 (4H); 2.5 (2H); 2.85 (2H); 3.7 (4H); 4.2 (2H); 6.9 (1 exch. H); 7–7.4 (9H).
In the same manner, there were obtained:
2-[3-[4-(ethoxycarbonylamino)phenyl]propyl]-2-phenyl-1,3-dioxolane (code number MD 360386)
¹H NMR (CDCl₃) δ ppm: 1.25 (3H); 1.4–2.2 (4H); 2.5 (2H); 3.5–4 (4H); 4.2 (2H); 6.6–7.6 (10H of which 1 exch.);
m.p.=66° C.
2-[3-[4-(ethoxycarbonylamino)phenyl]propyl]-2-cyclohexyl-1,3-dioxolane (code number MD 360420)
m.p.=70° C.
IR (KBr) $\nu$ cm⁻¹: 3360, 1705.

Step 7:
3-[4-[3-(2-phenylmethyl-1,3-dioxolane-2-yl)propyl]phenyl]-5(R)-methoxymethyl-2-oxazolidinone (code number MD 360334)

This compound is obtained by reacting at 160° C. for 3 hours of compound MD 360375 (3.6×10⁻³ mol), K₂CO₃ (0.72×10⁻³ mol) and compound MD 360287 (Example 15).
¹H NMR (CDCl₃) δ ppm: 1.6 (4H); 2.5 (2H); 2.85 (2H); 3.4 (3H); 3.45–4.2 (8H); 4.65 (1H); 6.9–7.6 (9H).
$[\alpha]_D^{20}$: −33.2° (c=1, CH₂Cl₂);

In the same manner, there were obtained:
3-[4-[3-(2-phenyl-1,3-dioxolane-2-yl)propyl]phenyl]-5(R)-methoxymethyl-2-oxazolidinone (code number MD 360332)
¹H NMR (CDCl₃) δ ppm: 1.4–2.1 (4H); 2.55 (2H); 3.4 (3H); 3.6 (2H); 3.6–4.2 (6H); 4.65 (1H); 6.95–7.95 (9H);
IR (KBr) $\nu$ cm⁻¹: 1750;
$[\alpha]_D^{20}$ = −31.9° (c=1, CH₂Cl₂)
3-[4-[3-(2-cyclohexyl-1,3-dioxolane-2-yl)propyl]phenyl]-5(R)-methoxymethyl-2-oxazolidinone (code number 360354)
m.p.=86° C.

EXAMPLE 14

3-[4-(5-phenyl-4-oxopentyl)phenyl]-5(R)-methoxymethyl-2-oxazolidinone (MD 360394)

This compound was obtained from compound MD 360334 (Example 13) subjected to the procedure of Method 2 of Example 4. Yield: 58%.; m.p. 105° C.;
$[\alpha]_D^{20}$: −35.9° (c=1, CH₂Cl₂);
¹H NMR (CDCl₃) δ ppm: 1.9 (2H); 2.5 (4H); 3.4 (3H); 3.6 (2H); 3.65 (2H); 3.95 (2H); 4.7 (1H); 7.1 (2H); 7.25 (5H); 7.45 (2H);
IR (KBr) $\nu$ cm⁻¹: 1740, 1710.
In the same manner, there were obtained, from the corresponding dioxolanes:
3-[4-(4-phenyl-4-oxobutyl)phenyl]-5(R)-methoxymethyl-2-oxazolidinone (MD 360401);
IR (microcell) $\nu$ cm⁻¹: 1750–1735
¹H NMR (CDCl₃) δ ppm: 2.05 (2H); 2.5–3.1 (4H); 3.4 (3H); 3.6 (2H); 3.8–4.2 (2H); 4.65 (1H); 7–7.6 (7H); 7.9 (2H);
m.p.=83° C.
3-[4-(4-cyclohexyl-4-oxobutyl)phenyl]-5(R)-methoxymethyl 2-oxazolidinone (code number 360399)
m.p.=80° C.;
¹H NMR (CDCl₃) δ ppm: 0.9–2.2 (13H); 2.2–2.7 (4H); 3.4 (3H); 3.6 (2H); 3.7–4.2 (2H); 4.6 (1H); 7.1 (2H); 7.4 (2H).

EXAMPLE 15

4-Methoxymethyl-1,3-dioxolane-2-one (S) (code number MD 360287)

A mixture of 14 g (0.132 mol) of 3-methoxypropane-1,2-diol (R) and of 31.16 g (0.264 mol) of diethyl carbonate in the presence of 0.108 g of 50% sodium hydride is heated until distillation of the alcohol formed. After completion of the reaction, the aimed product is distilled.
b.p.$_{0,3}$: 117° C.; Yield: 93%;
$[\alpha]_D^{20}$: −32.2° (c=1, CH₂Cl₂);
IR (microcell) $\nu$ cm⁻¹: 1790;
¹H NMR (CDCl₃) δ ppm: 3.4 (3H); 3.6 (2H); 4.3–4.9 (3H).

EXAMPLE 16

2-cyclohexyl-2-(2-bromoethyl)-1,3-dioxolane (code number 360414)

Step 1: 3-bromo-1-cyclohexyl-propanone

In a solution of 1-cyclohexyl-1-one-2-propene (0.255 mol) in 200 ml of CH₂Cl₂, cooled at 10°–15° C., HBr gas is bubbled through. After completion of the reaction, the reaction medium is washed with an aqueous NaHCO₃ saturated solution, dried over Na₂SO₄ and concentrated to obtain the aimed product as an oil.

Step 2: 2-cyclohexyl-2 (2-bromoethyl)-1,3 dioxolane

A solution of the compound obtained in the previous step (0.223 mol) in 600 ml of benzene, this solution further comprising 0.58 mol of ethylene glycol and 2.5 g of paratoluene sulphonic in acid is refluxed while removing the formed water. After 3 hours 30 min. of reaction, the solution is poured in a saturated NaCl solution, the organic phase is dried over $Na_2SO_4$, concentrated and purified by chromatography (silica, eluent: heptane 60 - $CH_2Cl_2$ 40).

EXAMPLE 17

Step 1: 2,2-Dimethyl-4(S)-methoxymethyl-dioxolane (code number 370486)

To 910 ml of water, are added 910 g of NaOH as tablet, and then, at room temperature, 5 l of $CH_2Cl_2$, 44.4 g (0.195 mol) of benzyl triethylammonium chloride, 8,558.6 g (6.5 mol) of 2,2-dimethyl-3(S)-hydroxymethyldioxolane and 1,229.5 g (9.75 mol) of dimethyl sulphate. The reaction medium is stirred for 12 h and poured on water. The organic phase is concentrated. The product is distilled.

b.p.$_{10}$=45° C.
$[\alpha]_D^{20}$= +7.9° (c=4, $CH_3OH$);
IR (microcell) $\nu$ cm$^{-1}$=2996, 2940, 2820, 1380, 1370, 840;
$^1$H NMR ($CDCl_3$) $\delta$ ppm =1.8 (3H); 1.4 (3H); 3.35 (3H); 3.4-4.4 (3H); 4 (2H). [J.A.C.S., 79, 1990 (1957)].

Step 2: 3-Methoxy-propane-1,2-diol (R) (code number 370487)

A solution of 950.3 g (6.5 mol) of compound 370486 in 450 ml of water is heated at 60° C. and 3.2 ml of concentrated hydrochloric acid and then 9 ml of triethylamine are added, and the reaction medium is concentrated and distilled with a 84% yield.

b.p.$_1$=66° C.
$[\alpha]_D^{20}$= -6.4° (C=4, $CH_3OH$);
IR (microcell) $\nu$ cm$^{-1}$: 3500-3300, 2960, 2945, 2910;
$^1$H NMR (DMSOd$_6$) $\delta$ ppm: 3.2-3.7 (8H); 4.5 (2 exch. H). [J.A.C.S., 79, 1990 (1957)]

EXAMPLE 18

3-[4-(3-oxo-1-pentenyl) phenyl]-5 (R)-methoxymethyl 2-oxazolidinone (code number 360 393)

Step 1:
3-[4-(2-methyl-1,3-dioxolane-2-yl-1-propenylene) phenyl]-5 (R)-methoxymethyl-2 oxazolidinone (code number 360392)

A mixture of 0.470 g ($2\times10^{-3}$ mol) of compound 230256 (ex. 12), 0.414 g ($3\times10^{-3}$ mol) of $K_2CO_3$, 1.14 g ($2.5\times10^{-3}$ mol) of the phosphonium compound used in step 1 of example 10 in solution in 2 ml of dioxane and 0.072 ml of water is heated at 80° C. for 3 h. The reaction mixture is poured on water and extracted with ethyl acetate. The organic phase is dried on $MgSO_4$ and concentrated. The product is obtained by chromatography (silica, eluent: heptane 40, ethyl acetate 60) with a yield of 31%.

$^1$HNMR ($CDCl_3$) $\delta$ ppm: 1.3 (3H); 2.6 (2H) 3.4 (3H); 3.6 (2H); 4 (6H); 4.7 (1H); 5.7 (1H); 6.4 (1H); 7.7-7.6 (4H).

Step 2: Compound of code number MD 360393

Obtained according to the procedure of method 2 of example 4:
IR (microcell) $\nu$ cm$^{-1}$: 1748, 1712, 1606;
$^1$HNMR ($CDCl_3$) $\delta$ ppm: 2.2 (3H); 3.4 (5H); 3.6 (2H); 3.9 (2H); 4.7 (1H); 5.7-6.8 (2H); 7.1-7.7 (4H).

The derivatives of formula (I) have been studied on experimental animals and showed pharmacological activities especially in the psychotropic field, particularly as potential antidepressants and anxiolytics.

The antidepressive activity has been demonstrated by the 5-HTP potentialisation assay in rat according to the procedure described by: M. JALFRE, B. BUCHER, A. COSTON, G. MOCQUET and R. D. PORSOLT: Arch. Int. Pharmacodyn. (1982), 259, 194–221. The dose of product which, when given orally, brings about in 50% of the animals (ED$_{50}$) the appearance of generalized shakings or of stereotypies (trinklings, shakes of head) consecutive to the administration by intraperitoneal route 1 h after the first treatment of 5-hydroxy-tryptophane (5-HTP) is determined in rat. The results obtained with some compounds according to the invention in the previously mentioned assay are set forth, by way of example, in the table below, in which is also mentioned the acute toxicity (LD$_{50}$) of some of the tested compounds and which is evaluated in mouse according to the method of J. T. LITCHFIELD and F. WILCOXON (J. Pharmacol. Exp. Ther. (1949), 96, 99).

TABLE

| TESTED COMPOUND CODE NUMBER | ED$_{50}$ mg/kg | LD$_{50}$mg/kg p.o. |
| --- | --- | --- |
| MD370268 | 0.72 | |
| MD370298 | 1.6 | |
| MD230050 | 1.2 | >3500 |
| MD230083 | 1.9 | |
| TOLOXATONE | 30 | |

The previously mentioned results show that the compounds which make the subject-matter of the present invention can be used for the preparation of psychotropic drugs and particularly potential antidepressants and anxiolytics, these drugs finding their use in therapy particularly for the treatment of endogenous and exogenous depressive states.

These drugs can be administred to humans or any warm-blooded animals in a variety of pharmaceutical forms well-known in the art and particularly in the form of compositions formulated for their administration by an oral, injectable or rectal route.

For the orally administration, said compositions can take the form of tablets, dragées or capsules prepared by the conventional techniques using known carriers and excipients, such as binding agents, fillers, lubricants and desintegration agents; they can also be in the form of solutions, syrups or suspensions.

For the administration in the form of an injectable solute, the compositions according to the invention may be in the form of injectable solutions, suspensions or emulsions containing an acceptable oily or aqueous liquid carrier.

For the rectal administration, the compositions may be in the form of suppositories containing the conventional bases for suppositories.

The therapeutic active dose of the active principles, i.e. of the derivatives (I) and of the pharmaceutically acceptable salts thereof, depends particularly on the administration route, the patient's body weight and on the therapeutic potency of the used active principles.

By oral route, the given doses may generally reach 10 mg/kg/day of active principle (in one or more intakes); by injectable route, they may reach 1 mg/kg/day (in one or more intakes); by rectal route, they may reach 5 mg/kg/day of active compound (in one or more suppositories).

We claim:

1. A compound of the formula:

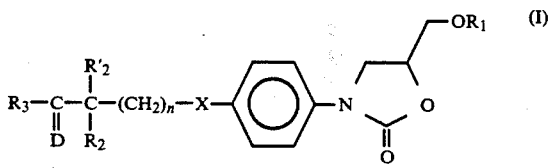

$R_1$ is H or $C_1$-$C_4$ alkyl;

X is a methylene group or a —CH=CH— group;

n is 1 or 2 when x is a methylene group and 0 or 1 when X a —CH=CH— group;

D is an oxygen atom or a NOR group, wherein R=H or $C_1$-$C_4$ alkyl;

$R_3$ is a $C_1$-$C_4$ alkyl, $C_3$-$C_7$ cycloalkyl, phenyl or benzyl group;

each of $R_2$ and $R'_2$ independently is a hydrogen atom or a $C_1$-$C_4$ alkyl, $C_3$-$C_7$ cycloalkyl, phenyl or benzyl group; and $R'_2$ and $R_3$ may further form together a —$(CH_2)_3$— or —$(CH_2)_4$— chain, said compounds being in the form of diastereoisomers or enantiomers or in the cis- or trans-form or in the form of a mixture thereof, including the racemic forms.

2. A compound according to claim 1, wherein:
$R_1$=H or $CH_3$;
X=$CH_2$;
n=1 or 2;
$R_2$=$R'_2$=H or $CH_3$;
$R_3$=$C_1$-$C_4$ alkyl; and
D is oxygen, N—OH or N—OCH$_3$.

3. A compound according to claim 1, having one asymmetric carbon atom, wherein:
$R_1$=$CH_3$;
X=methylene;
n=1 or 2;
$R_2$=$R'_2$=H;
$R_3$=$CH_3$; and
D is oxygen.

4. A compound according to claim 1, having one asymmetric carbon atom, wherein:
$R_1$=$CH_3$;
X=methylene;
n=1 or 2;
$R_2$=$R'_2$=H
$R_3$=$CH_3$; and D is (E)N—OH.

5. A compound according to claim 1, having one asymmetric carbon atom, wherein:
$R_1$=$CH_3$;
X is CH=CH;
n=0 or 1;
$R_2$=$R'_2$=H;
$R_3$=$CH_3$; and pl D is oxygen.

6. A compound according to claim 1 having one asymmetric carbon atom wherein:
$R_1$=$CH_3$;
X is CH=CH;
n is 0 or 1;
$R_2$=$R'_2$=H;
$R_3$=$CH_3$; and
D is (E) N—OH.

7. A compound according to claim 1 having asymmetric carbon atom wherein $R_1$=$CH_3$; X=methylene; n=1; $R_2$=$R'_2$=H; $R_3$=$CH_3$; and D is oxygen.

8. A compound according to claims 3, 4, 5, 6 or 7, wherein the asymmetric carbon atom has the (R) configuration.

9. A pharmaceutical composition, characterized in that it contains a physiologically acceptable excipient and at least a compound selected among the compounds according to claims 1, 2, 3, 4, 5, 6 or 7.

10. A method for the treatment of anxiety and endogenous or exogenous depressive states in warm-blooded animals, which comprises internally administering thereto an anxiolytic or antidepressive effective amount of a compound of formula (I):

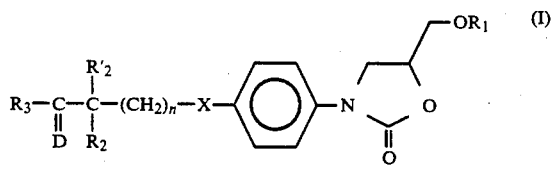

wherein:
$R_1$ is H or $C_1$-$C_4$ alkyl;
X is a methylene group or a —CH=CH— group;
n is 1 or 2 when X is a methylene group and 0 or 1 when X is a —CH=CH— group;
D is an oxygen atom or a NOR group, wherein R=H or $C_1$-$C_4$ alkyl;
$R_3$ is a $C_1$-$C_4$ alkyl, $C_3$-$C_7$ cycloalkyl, phenyl or benzyl group;
each of $R_2$ and $R'_2$ independently is a hydrogen atom or a $C_1$-$C_4$ alkyl, $C_3$-$C_7$ cycloalkyl, phenyl or benzyl group; and
$R'_2$ and $R_3$ may further form together a —$(CH_2)_3$— or —$(CH_2)_4$— chain, said compounds being in the form of diastereosiomers or enantiomers or in the cis- or trans-form or in the form of a mixture thereof, including the racemic forms.

* * * * *